(12) United States Patent
Alberti et al.

(10) Patent No.: US 8,870,812 B2
(45) Date of Patent: Oct. 28, 2014

(54) DIALYSIS SYSTEM HAVING VIDEO DISPLAY WITH AMBIENT LIGHT ADJUSTMENT

(75) Inventors: James J. Alberti, Odessa, FL (US); Rick Gilbert, Clearwater, FL (US); Pete Hopping, Lutz, FL (US); John Bedingfield, Largo, FL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 1073 days.

(21) Appl. No.: 11/675,492

(22) Filed: Feb. 15, 2007

(65) Prior Publication Data
US 2008/0200868 A1   Aug. 21, 2008

(51) Int. Cl.
*A61M 1/00* (2006.01)
*A61M 1/28* (2006.01)
*G09G 3/34* (2006.01)

(52) U.S. Cl.
CPC .......... *A61M 1/28* (2013.01); *A61M 1/288* (2014.02); *G09G 3/3406* (2013.01); *A61M 2205/505* (2013.01); *A61M 2205/502* (2013.01); *G09G 2360/144* (2013.01); *G09G 2320/0626* (2013.01); *A61M 2205/12* (2013.01)
USPC ............... 604/29; 345/207; 345/102

(58) Field of Classification Search
USPC .............. 604/29, 131; 345/207, 102
See application file for complete search history.

(56) References Cited

U.S. PATENT DOCUMENTS

| | | | |
|---|---|---|---|
| 2,705,223 A | 3/1955 | Renfrew et al. | |
| 2,971,876 A | 2/1961 | Phair | |
| 3,255,923 A | 6/1966 | Soto | |
| 3,375,300 A | 3/1968 | Ropp | |
| 3,428,828 A | 2/1969 | Korzekwa et al. | |
| 3,494,897 A | 2/1970 | Reding et al. | |
| 3,507,708 A | 4/1970 | Vingnaud | |
| 3,514,359 A | 5/1970 | Frese | |
| 3,561,493 A | 2/1971 | Maillard | |
| 3,645,992 A | 2/1972 | Elston | |
| 3,772,136 A | 11/1973 | Workman | |
| 3,814,799 A | 6/1974 | Wygasch | |
| 3,816,033 A | 6/1974 | Fried et al. | |

(Continued)

FOREIGN PATENT DOCUMENTS

| | | |
|---|---|---|
| DE | 251 904 | 2/1967 |
| DE | 1964735 | 7/1971 |

(Continued)

OTHER PUBLICATIONS

U.S. Appl. No. 11/675,495, filed Feb. 15, 2007, Bedingfield.

(Continued)

*Primary Examiner* — Kevin C Sirmons
*Assistant Examiner* — Deanna K Hall
(74) *Attorney, Agent, or Firm* — K&L Gates LLP

(57) ABSTRACT

A medical therapy machine includes: an enclosure; a medical therapy machine component located inside the enclosure; a video monitor supported by the enclosure and displaying at least one of information and indicia relating to the medical therapy; an ambient light sensor positioned with respect to the enclosure so as to be able to sense a level of ambient light impinging the enclosure; and a logic implementor configured to control a level of backlight brightness for the video monitor based on the level of ambient light sensed by the sensor.

30 Claims, 19 Drawing Sheets

(56) References Cited

U.S. PATENT DOCUMENTS

| | | |
|---|---|---|
| 3,858,581 A | 1/1975 | Kamen |
| 3,912,843 A | 10/1975 | Brazier |
| 3,937,758 A | 2/1976 | Castagna |
| 3,995,084 A | 11/1976 | Berger et al. |
| 4,041,103 A | 8/1977 | Davison et al. |
| 4,058,647 A | 11/1977 | Inoue et al. |
| 4,071,040 A | 1/1978 | Moriarty |
| 4,087,587 A | 5/1978 | Shida et al. |
| 4,087,588 A | 5/1978 | Shida et al. |
| 4,095,012 A | 6/1978 | Schirmer |
| 4,110,303 A | 8/1978 | Gergen et al. |
| 4,122,947 A | 10/1978 | Falla |
| 4,137,915 A | 2/1979 | Kamen |
| 4,140,118 A | 2/1979 | Jassawalla |
| 4,142,524 A | 3/1979 | Jassawalla et al. |
| 4,147,827 A | 4/1979 | Breidt, Jr. et al. |
| 4,181,245 A | 1/1980 | Garrett et al. |
| 4,187,057 A | 2/1980 | Xanthopoulos |
| 4,211,519 A | 7/1980 | Hogan |
| 4,233,367 A | 11/1980 | Ticknor et al. |
| 4,236,880 A | 12/1980 | Archibald |
| 4,243,619 A | 1/1981 | Fraser et al. |
| 4,265,601 A | 5/1981 | Mandroian |
| 4,286,597 A | 9/1981 | Gajewski |
| 4,298,714 A | 11/1981 | Levin et al. |
| 4,303,376 A | 12/1981 | Siekmann |
| 4,322,465 A | 3/1982 | Webster |
| 4,322,480 A | 3/1982 | Tuller et al. |
| D264,134 S | 4/1982 | Xanthopoulos |
| 4,327,726 A | 5/1982 | Kwong et al. |
| 4,332,655 A | 6/1982 | Berejka |
| 4,333,088 A | 6/1982 | Diggins |
| 4,336,352 A | 6/1982 | Sakurai et al. |
| 4,381,005 A | 4/1983 | Bujan |
| 4,382,753 A | 5/1983 | Archibald |
| 4,387,184 A | 6/1983 | Coquard et al. |
| 4,391,600 A | 7/1983 | Archibald |
| 4,405,667 A | 9/1983 | Christensen et al. |
| 4,405,774 A | 9/1983 | Miwa et al. |
| 4,407,877 A | 10/1983 | Rasmussen |
| 4,407,888 A | 10/1983 | Crofts |
| 4,410,164 A | 10/1983 | Kamen |
| 4,410,322 A | 10/1983 | Archibald |
| 4,411,649 A | 10/1983 | Kamen |
| 4,417,753 A | 11/1983 | Bacehowski |
| 4,429,076 A | 1/1984 | Saito et al. |
| 4,438,238 A | 3/1984 | Fukushima et al. |
| 4,449,976 A | 5/1984 | Kamen |
| 4,472,116 A | 9/1984 | Wenstrup |
| 4,472,117 A | 9/1984 | Wenstrup |
| 4,473,342 A | 9/1984 | Iles |
| 4,479,760 A | 10/1984 | Bilstad et al. |
| 4,479,761 A | 10/1984 | Bilstad et al. |
| 4,479,762 A | 10/1984 | Bilstad et al. |
| 4,479,989 A | 10/1984 | Mahal |
| 4,521,437 A | 6/1985 | Storms |
| 4,537,561 A | 8/1985 | Xanthopoulos |
| 4,547,136 A | 10/1985 | Rothstein |
| 4,548,348 A | 10/1985 | Clements |
| 4,562,118 A | 12/1985 | Maruhashi et al. |
| 4,568,723 A | 2/1986 | Lu |
| 4,573,994 A | 3/1986 | Fischell et al. |
| 4,574,173 A | 3/1986 | Bennett |
| 4,586,920 A | 5/1986 | Peabody |
| 4,588,648 A | 5/1986 | Krueger |
| 4,599,055 A | 7/1986 | Dykstra |
| 4,599,276 A | 7/1986 | Martini |
| 4,600,401 A | 7/1986 | Kamen |
| 4,620,690 A | 11/1986 | Kamen |
| 4,627,844 A | 12/1986 | Schmitt |
| 4,628,969 A | 12/1986 | Jurgens, Jr. et al. |
| 4,634,426 A | 1/1987 | Kamen |
| 4,636,412 A | 1/1987 | Field |
| 4,640,870 A | 2/1987 | Akazawa et al. |
| 4,642,098 A | 2/1987 | Lundquist |
| 4,643,926 A | 2/1987 | Mueller |
| 4,648,872 A | 3/1987 | Kamen |
| 4,657,490 A | 4/1987 | Abbott |
| 4,668,752 A | 5/1987 | Tominari et al. |
| 4,673,334 A | 6/1987 | Allington et al. |
| 4,681,797 A | 7/1987 | Van Iseghem |
| 4,686,125 A | 8/1987 | Johnston et al. |
| 4,692,361 A | 9/1987 | Johnston et al. |
| 4,696,671 A | 9/1987 | Epstein et al. |
| 4,707,389 A | 11/1987 | Ward |
| 4,724,028 A | 2/1988 | Zabielski et al. |
| 4,726,997 A | 2/1988 | Mueller et al. |
| 4,732,795 A | 3/1988 | Ohya et al. |
| 4,734,327 A | 3/1988 | Vicik |
| 4,735,558 A | 4/1988 | Kienholz et al. |
| 4,735,855 A | 4/1988 | Wofford et al. |
| 4,740,582 A | 4/1988 | Coquard et al. |
| 4,749,109 A | 6/1988 | Kamen |
| 4,753,222 A | 6/1988 | Morishita |
| 4,760,114 A | 7/1988 | Haaf et al. |
| 4,762,864 A | 8/1988 | Goel et al. |
| 4,764,404 A | 8/1988 | Genske et al. |
| 4,767,377 A | 8/1988 | Falla |
| 4,767,651 A | 8/1988 | Starczweski et al. |
| 4,772,497 A | 9/1988 | Maasola |
| 4,778,450 A | 10/1988 | Kamen |
| 4,778,451 A | 10/1988 | Kamen |
| 4,778,697 A | 10/1988 | Genske et al. |
| 4,786,697 A | 11/1988 | Cozewith et al. |
| 4,789,714 A | 12/1988 | Cozewith et al. |
| 4,792,488 A | 12/1988 | Schirmer |
| 4,794,942 A | 1/1989 | Yasuda et al. |
| 4,795,782 A | 1/1989 | Lutz et al. |
| 4,798,580 A | 1/1989 | DeMeo et al. |
| 4,800,129 A | 1/1989 | Deak |
| 4,803,102 A | 2/1989 | Raniere et al. |
| 4,808,161 A | 2/1989 | Kamen |
| 4,816,343 A | 3/1989 | Mueller |
| 4,818,190 A | 4/1989 | Pelmulder et al. |
| 4,824,339 A | 4/1989 | Bainbridge et al. |
| 4,826,482 A | 5/1989 | Kamen |
| 4,834,755 A | 5/1989 | Silvestrini et al. |
| 4,842,948 A | 6/1989 | Gagliani et al. |
| 4,848,722 A | 7/1989 | Webster |
| 4,852,851 A | 8/1989 | Webster |
| 4,855,356 A | 8/1989 | Holub et al. |
| 4,856,259 A | 8/1989 | Woo et al. |
| 4,856,260 A | 8/1989 | Woo et al. |
| 4,861,242 A | 8/1989 | Finsterwald |
| 4,863,996 A | 9/1989 | Nakazima et al. |
| 4,871,799 A | 10/1989 | Kobayashi et al. |
| 4,872,813 A | 10/1989 | Gorton et al. |
| 4,873,287 A | 10/1989 | Holub et al. |
| 4,877,682 A | 10/1989 | Sauers et al. |
| 4,885,119 A | 12/1989 | Mueller et al. |
| 4,886,431 A | 12/1989 | Soderquist et al. |
| 4,904,168 A | 2/1990 | Cavoto et al. |
| 4,910,085 A | 3/1990 | Raniere et al. |
| 4,923,470 A | 5/1990 | Dumican |
| 4,929,479 A | 5/1990 | Shishido et al. |
| 4,931,520 A | 6/1990 | Yamanashi et al. |
| 4,937,299 A | 6/1990 | Ewen et al. |
| 4,941,519 A | 7/1990 | Sestak et al. |
| 4,946,616 A | 8/1990 | Falla et al. |
| 4,950,720 A | 8/1990 | Randall, Jr. et al. |
| 4,957,966 A | 9/1990 | Nishio et al. |
| 4,957,967 A | 9/1990 | Mizuno et al. |
| 4,966,795 A | 10/1990 | Genske et al. |
| 4,976,162 A | 12/1990 | Kamen |
| 4,977,213 A | 12/1990 | Giroud-Abel et al. |
| 4,990,054 A | 2/1991 | Janocko |
| 4,992,511 A | 2/1991 | Yamamoto et al. |
| 4,996,054 A | 2/1991 | Pietsch et al. |
| 4,999,254 A | 3/1991 | Ofstein |
| 5,003,019 A | 3/1991 | Ishimaru et al. |
| 5,006,601 A | 4/1991 | Lutz et al. |
| 5,008,204 A | 4/1991 | Stehling |
| 5,008,356 A | 4/1991 | Ishimaru et al. |
| 5,017,652 A | 5/1991 | Abe et al. |

(56) References Cited

U.S. PATENT DOCUMENTS

| | | |
|---|---|---|
| 5,019,140 A | 5/1991 | Bowser et al. |
| 5,034,457 A | 7/1991 | Serini et al. |
| 5,034,458 A | 7/1991 | Serini et al. |
| 5,043,088 A | 8/1991 | Falla |
| 5,044,902 A | 9/1991 | Malbec |
| 5,053,457 A | 10/1991 | Lee |
| 5,062,774 A | 11/1991 | Kramer et al. |
| 5,071,686 A | 12/1991 | Genske et al. |
| 5,071,911 A | 12/1991 | Furuta et al. |
| 5,071,912 A | 12/1991 | Furuta et al. |
| 5,075,376 A | 12/1991 | Furuta et al. |
| 5,079,295 A | 1/1992 | Furuta et al. |
| 5,085,649 A | 2/1992 | Flynn |
| 5,087,677 A | 2/1992 | Brekner et al. |
| 5,088,515 A | 2/1992 | Kamen |
| 5,093,164 A | 3/1992 | Bauer et al. |
| 5,093,194 A | 3/1992 | Touhsaent et al. |
| 5,094,820 A | 3/1992 | Maxwell et al. |
| 5,094,921 A | 3/1992 | Itamura et al. |
| 5,098,262 A | 3/1992 | Wecker et al. |
| 5,106,366 A | 4/1992 | Steppe |
| 5,108,844 A | 4/1992 | Blumberg et al. |
| 5,110,642 A | 5/1992 | Genske et al. |
| 5,116,906 A | 5/1992 | Mizuno et al. |
| 5,125,891 A | 6/1992 | Hossain et al. |
| 5,129,894 A | 7/1992 | Sommermeyer et al. |
| 5,132,363 A | 7/1992 | Furuta et al. |
| 5,133,650 A | 7/1992 | Sunderland et al. |
| 5,135,485 A | 8/1992 | Cohen et al. |
| 5,135,785 A | 8/1992 | Milton |
| 5,145,731 A | 9/1992 | Lund et al. |
| 5,154,979 A | 10/1992 | Kerschbaumer et al. |
| 5,159,004 A | 10/1992 | Furuta et al. |
| 5,164,267 A | 11/1992 | D'Heur et al. |
| 5,176,634 A | 1/1993 | Smith et al. |
| 5,176,956 A | 1/1993 | Jevne et al. |
| 5,178,182 A | 1/1993 | Kamen |
| 5,183,706 A | 2/1993 | Bekele |
| 5,185,084 A | 2/1993 | Lapidus et al. |
| 5,185,189 A | 2/1993 | Stenger et al. |
| 5,189,091 A | 2/1993 | Laughner |
| 5,193,913 A | 3/1993 | Rosenbaum |
| 5,193,990 A | 3/1993 | Kamen et al. |
| 5,194,316 A | 3/1993 | Horner et al. |
| 5,195,960 A | 3/1993 | Hossain et al. |
| 5,195,986 A | 3/1993 | Kamen |
| 5,196,254 A | 3/1993 | Alliyama |
| 5,203,943 A | 4/1993 | Nornberg et al. |
| 5,206,290 A | 4/1993 | Mizuno et al. |
| 5,207,983 A | 5/1993 | Liebert et al. |
| 5,211,201 A | 5/1993 | Kamen et al. |
| 5,212,238 A | 5/1993 | Schelbelhoffer et al. |
| 5,213,483 A | 5/1993 | Flaherty et al. |
| 5,215,312 A | 6/1993 | Knappe et al. |
| 5,218,048 A | 6/1993 | Abe et al. |
| 5,218,049 A | 6/1993 | Yamamoto et al. |
| 5,222,946 A | 6/1993 | Kamen |
| 5,230,934 A | 7/1993 | Sakano et al. |
| 5,230,935 A | 7/1993 | Delimoy et al. |
| 5,238,997 A | 8/1993 | Bauer et al. |
| 5,241,985 A | 9/1993 | Faust et al. |
| 5,244,971 A | 9/1993 | Dekonick |
| 5,245,151 A | 9/1993 | Chamberlain et al. |
| 5,252,044 A | 10/1993 | Raines et al. |
| 5,254,824 A | 10/1993 | Chamberlain et al. |
| 5,257,917 A | 11/1993 | Minarik et al. |
| 5,258,230 A | 11/1993 | La Fleur et al. |
| 5,272,235 A | 12/1993 | Wakatsuru et al. |
| 5,278,231 A | 1/1994 | Chundury |
| 5,278,377 A | 1/1994 | Tsai |
| 5,288,531 A | 2/1994 | Falla et al. |
| 5,288,560 A | 2/1994 | Sudo et al. |
| 5,288,799 A | 2/1994 | Schmidt et al. |
| 5,290,856 A | 3/1994 | Okamoto |
| 5,294,763 A | 3/1994 | Chamberlain et al. |
| 5,302,093 A | 4/1994 | Owens et al. |
| 5,306,542 A | 4/1994 | Bayer |
| 5,312,867 A | 5/1994 | Mitsuno et al. |
| 5,317,059 A | 5/1994 | Chundury et al. |
| 5,331,057 A | 7/1994 | Brekner et al. |
| 5,336,190 A | 8/1994 | Moss et al. |
| 5,342,886 A | 8/1994 | Glotin et al. |
| 5,348,794 A | 9/1994 | Takahashi |
| 5,350,357 A | 9/1994 | Kamen et al. |
| 5,356,676 A | 10/1994 | Von Widdern et al. |
| 5,359,001 A | 10/1994 | Epple et al. |
| 5,360,648 A | 11/1994 | Falla et al. |
| 5,364,371 A | 11/1994 | Kamen |
| 5,364,486 A | 11/1994 | Falla et al. |
| 5,371,151 A | 12/1994 | Berge et al. |
| 5,378,543 A | 1/1995 | Muruta et al. |
| 5,378,800 A | 1/1995 | Mok et al. |
| 5,382,630 A | 1/1995 | Stehling et al. |
| 5,382,631 A | 1/1995 | Stehling et al. |
| 5,385,540 A | 1/1995 | Abbott et al. |
| 5,387,645 A | 2/1995 | Montag et al. |
| 5,397,222 A | 3/1995 | Moss et al. |
| 5,401,342 A | 3/1995 | Vincent et al. |
| 5,409,355 A | 4/1995 | Brooke |
| 5,421,823 A | 6/1995 | Kamen et al. |
| 5,422,409 A | 6/1995 | Brekner et al. |
| 5,427,509 A | 6/1995 | Chapman et al. |
| 5,429,485 A | 7/1995 | Dodge |
| 5,431,626 A | 7/1995 | Bryant et al. |
| 5,433,588 A | 7/1995 | Monk et al. |
| 5,438,510 A | 8/1995 | Bryant et al. |
| 5,439,587 A | 8/1995 | Stankowski et al. |
| 5,442,919 A | 8/1995 | Wilhelm |
| 5,445,506 A | 8/1995 | Afflerbaugh et al. |
| 5,446,270 A | 8/1995 | Chamberlain et al. |
| 5,457,249 A | 10/1995 | Toshihiro et al. |
| 5,460,490 A | 10/1995 | Carr et al. |
| 5,460,493 A | 10/1995 | Deniega et al. |
| 5,462,416 A | 10/1995 | Dennehy et al. |
| 5,464,388 A | 11/1995 | Merte et al. |
| 5,474,683 A | 12/1995 | Bryant et al. |
| 5,475,060 A | 12/1995 | Brekner et al. |
| 5,480,294 A | 1/1996 | Di Perna et al. |
| 5,482,440 A | 1/1996 | Dennehey et al. |
| 5,482,770 A | 1/1996 | Bekele |
| 5,487,649 A | 1/1996 | Dorsey, III et al. |
| 5,498,677 A | 3/1996 | Weller |
| 5,508,051 A | 4/1996 | Falla et al. |
| 5,518,378 A | 5/1996 | Neftel et al. |
| 5,522,769 A | 6/1996 | DeGuiseppi |
| 5,525,659 A | 6/1996 | Falla et al. |
| 5,526,844 A | 6/1996 | Kamen |
| 5,529,708 A | 6/1996 | Palmgren et al. |
| 5,530,065 A | 6/1996 | Farley et al. |
| 5,533,589 A | 7/1996 | Kamen et al. |
| 5,534,606 A | 7/1996 | Bennett et al. |
| 5,540,808 A | 7/1996 | Vincent et al. |
| 5,542,919 A | 8/1996 | Simon et al. |
| 5,552,504 A | 9/1996 | Bennett et al. |
| 5,554,013 A | 9/1996 | Owens et al. |
| 5,569,026 A | 10/1996 | Novak |
| 5,570,716 A | 11/1996 | Kamen et al. |
| 5,575,310 A | 11/1996 | Kamen et al. |
| 5,575,632 A | 11/1996 | Morris et al. |
| 5,578,012 A | 11/1996 | Kamen et al. |
| 5,580,914 A | 12/1996 | Falla et al. |
| 5,583,192 A | 12/1996 | Bennett et al. |
| 5,586,868 A | 12/1996 | Lawless et al. |
| 5,588,815 A | 12/1996 | Zaleski, II |
| 5,588,816 A | 12/1996 | Abbott et al. |
| 5,601,420 A | 2/1997 | Warner et al. |
| 5,609,572 A | 3/1997 | Lang |
| 5,610,253 A | 3/1997 | Hatke et al. |
| 5,620,312 A * | 4/1997 | Hyman et al. ............... 417/474 |
| 5,620,425 A | 4/1997 | Heffernan et al. |
| 5,628,908 A | 5/1997 | Kamen et al. |
| 5,629,398 A | 5/1997 | Okamoto et al. |
| 5,634,896 A | 6/1997 | Bryant et al. |
| 5,637,100 A | 6/1997 | Sudo |

(56) References Cited

U.S. PATENT DOCUMENTS

| | | | |
|---|---|---|---|
| 5,637,400 A | 6/1997 | Brekner et al. | |
| 5,650,471 A | 7/1997 | Abe et al. | |
| 5,655,897 A | 8/1997 | Neftel et al. | |
| 5,674,944 A | 10/1997 | Falla et al. | |
| 5,676,530 A | 10/1997 | Nazarifar | |
| 5,686,527 A | 11/1997 | Laurin et al. | |
| 5,693,728 A | 12/1997 | Okamoto et al. | |
| 5,698,645 A | 12/1997 | Weller et al. | |
| 5,698,654 A | 12/1997 | Nye et al. | |
| 5,707,751 A | 1/1998 | Garza et al. | |
| 5,711,654 A | 1/1998 | Afflerbaugh | |
| 5,718,569 A | 2/1998 | Holst | |
| 5,721,025 A | 2/1998 | Falla et al. | |
| 5,723,189 A | 3/1998 | Sudo | |
| 5,733,991 A | 3/1998 | Rohrman et al. | |
| 5,741,125 A | 4/1998 | Neftel et al. | |
| 5,744,664 A | 4/1998 | Brekner et al. | |
| 5,752,813 A | 5/1998 | Tyner et al. | |
| 5,756,623 A | 5/1998 | Krueder et al. | |
| 5,760,760 A * | 6/1998 | Helms | 345/102 |
| 5,782,575 A | 7/1998 | Vincent et al. | |
| 5,788,670 A | 8/1998 | Reinhard et al. | |
| 5,788,671 A | 8/1998 | Johnson | |
| 5,792,824 A | 8/1998 | Natori | |
| 5,795,945 A | 8/1998 | Natori | |
| 5,816,779 A | 10/1998 | Lawless et al. | |
| 5,849,843 A | 12/1998 | Laurin et al. | |
| 5,854,347 A | 12/1998 | Laurin et al. | |
| 5,854,349 A | 12/1998 | Abe et al. | |
| 5,863,986 A | 1/1999 | Herrmann-Schonherr et al. | |
| 5,871,566 A | 2/1999 | Rutz | |
| 5,872,201 A | 2/1999 | Cheung et al. | |
| 5,879,768 A | 3/1999 | Falla et al. | |
| 5,899,674 A | 5/1999 | Jung et al. | |
| 5,906,598 A | 5/1999 | Giesler et al. | |
| 5,927,956 A | 7/1999 | Lim et al. | |
| 5,928,196 A | 7/1999 | Johnson et al. | |
| 5,931,808 A | 8/1999 | Pike | |
| 5,942,579 A | 8/1999 | Falla et al. | |
| 5,980,495 A | 11/1999 | Heinz et al. | |
| 5,983,136 A | 11/1999 | Kamen | |
| 5,984,762 A | 11/1999 | Tedeschi et al. | |
| 5,989,423 A | 11/1999 | Kamen et al. | |
| 5,990,254 A | 11/1999 | Weller et al. | |
| 5,993,949 A | 11/1999 | Rosenbaum et al. | |
| 5,998,019 A | 12/1999 | Rosenbaum et al. | |
| 6,001,201 A | 12/1999 | Vincent et al. | |
| 6,007,520 A | 12/1999 | Sudo | |
| 6,020,444 A | 2/2000 | Riedel et al. | |
| 6,036,458 A | 3/2000 | Cole et al. | |
| 6,045,648 A | 4/2000 | Palmgren et al. | |
| 6,056,522 A | 5/2000 | Johnson | |
| 6,059,544 A | 5/2000 | Jung et al. | |
| 6,060,572 A | 5/2000 | Gillis et al. | |
| 6,065,270 A | 5/2000 | Reinhard et al. | |
| 6,068,936 A | 5/2000 | Pfeiffer et al. | |
| 6,070,761 A | 6/2000 | Bloom et al. | |
| 6,074,183 A | 6/2000 | Allen et al. | |
| 6,077,246 A | 6/2000 | Kullas et al. | |
| 6,106,948 A | 8/2000 | Wang et al. | |
| 6,109,895 A | 8/2000 | Ray et al. | |
| 6,110,549 A | 8/2000 | Hamada et al. | |
| 6,110,617 A | 8/2000 | Feres | |
| 6,114,457 A | 9/2000 | Markel et al. | |
| 6,117,465 A | 9/2000 | Falla et al. | |
| 6,121,394 A | 9/2000 | Sugimoto et al. | |
| 6,129,699 A | 10/2000 | Haight et al. | |
| 6,136,744 A | 10/2000 | Gillis et al. | |
| 6,147,025 A | 11/2000 | Gillis et al. | |
| 6,165,154 A | 12/2000 | Gray et al. | |
| 6,168,862 B1 | 1/2001 | Rosenbaum et al. | |
| 6,169,052 B1 | 1/2001 | Brekner et al. | |
| 6,171,670 B1 | 1/2001 | Sudo et al. | |
| 6,186,752 B1 | 2/2001 | Deniega et al. | |
| 6,191,254 B1 | 2/2001 | Falla et al. | |
| 6,203,296 B1 | 3/2001 | Ray et al. | |
| 6,210,361 B1 | 4/2001 | Kamen et al. | |
| 6,221,648 B1 | 4/2001 | Le Page et al. | |
| 6,225,426 B1 | 5/2001 | Gillis et al. | |
| 6,225,427 B1 | 5/2001 | Burton et al. | |
| 6,231,320 B1 | 5/2001 | Lawless et al. | |
| 6,234,997 B1 | 5/2001 | Kamen et al. | |
| RE37,208 E | 6/2001 | Winter et al. | |
| 6,248,093 B1 | 6/2001 | Moberg | |
| 6,255,396 B1 | 7/2001 | Ding et al. | |
| 6,261,655 B1 | 7/2001 | Rosenbaum et al. | |
| 6,266,664 B1 | 7/2001 | Russell-Falla et al. | |
| 6,280,408 B1 | 8/2001 | Sipin | |
| 6,293,926 B1 | 9/2001 | Sorensen et al. | |
| 6,302,653 B1 | 10/2001 | Bryant et al. | |
| 6,343,614 B1 | 2/2002 | Gray et al. | |
| 6,364,857 B1 | 4/2002 | Gray et al. | |
| 6,372,848 B1 | 4/2002 | Yang et al. | |
| 6,382,923 B1 | 5/2002 | Gray | |
| 6,416,293 B1 | 7/2002 | Bouchard | |
| 6,468,242 B1 | 10/2002 | Wilson et al. | |
| 6,497,676 B1 | 12/2002 | Childers et al. | |
| 6,503,062 B1 | 1/2003 | Gray et al. | |
| 6,592,542 B2 | 7/2003 | Childers et al. | |
| 6,737,629 B2 * | 5/2004 | Nixon et al. | 250/214 C |
| 6,808,369 B2 | 10/2004 | Gray et al. | |
| 6,814,547 B2 | 11/2004 | Childers et al. | |
| 6,869,538 B2 | 3/2005 | Yu et al. | |
| 7,033,539 B2 | 4/2006 | Krensky et al. | |
| 7,117,019 B2 * | 10/2006 | Abbasi | 455/566 |
| 7,268,775 B1 * | 9/2007 | Gettemy | 345/204 |
| 7,410,475 B2 | 8/2008 | Krensky et al. | |
| 2002/0077598 A1 | 6/2002 | Yap et al. | |
| 2003/0195454 A1 | 10/2003 | Wariar et al. | |
| 2003/0204162 A1 | 10/2003 | Childers et al. | |
| 2003/0220609 A1 * | 11/2003 | Childers et al. | 604/29 |
| 2004/0254513 A1 | 12/2004 | Shang et al. | |
| 2005/0118038 A1 | 6/2005 | Grey et al. | |
| 2006/0007223 A1 | 1/2006 | Parker | |
| 2006/0181552 A1 * | 8/2006 | Hopple | 345/690 |
| 2008/0186707 A1 * | 8/2008 | Ku et al. | 362/253 |
| 2008/0200865 A1 | 8/2008 | Bedingfield | |
| 2008/0200866 A1 | 8/2008 | Prisco et al. | |
| 2008/0200867 A1 | 8/2008 | Bedingfield | |
| 2008/0200869 A1 | 8/2008 | Bedingfield | |

FOREIGN PATENT DOCUMENTS

| | | |
|---|---|---|
| DE | 133 411 | 1/1979 |
| DE | 39 37 865 | 6/1990 |
| EP | 0028371 | 5/1981 |
| EP | 0 156 464 A1 | 10/1985 |
| EP | 0204260 | 12/1986 |
| EP | 0 291 208 A2 | 11/1988 |
| EP | 0 306 664 | 3/1989 |
| EP | 0319272 | 6/1989 |
| EP | 0402505 | 12/1990 |
| EP | 0011935 | 5/1991 |
| EP | 0 216 509 B1 | 9/1991 |
| EP | 0248632 | 4/1992 |
| EP | 0 497 567 A2 | 8/1992 |
| EP | 0 524 802 A1 | 1/1993 |
| EP | 0 283 164 B1 | 5/1995 |
| EP | 0 492 982 B1 | 8/1995 |
| EP | 0 430 585 B1 | 1/1996 |
| EP | 0 156 464 B1 | 5/1996 |
| EP | 0 582 355 B1 | 5/1996 |
| EP | 0 709 105 | 5/1996 |
| EP | 0 203 799 B1 | 8/1996 |
| EP | 0 384 694 B1 | 9/1996 |
| EP | 0 497 567 B1 | 9/1996 |
| EP | 0 291 208 B1 | 8/1997 |
| EP | 0 790 063 A1 | 8/1997 |
| EP | 0 680 401 B1 | 1/1999 |
| FR | 2371931 | 6/1978 |
| FR | 2440740 | 6/1980 |
| GB | 1326236 | 8/1973 |
| GB | 2285329 | 7/1995 |
| JP | 03-095286 | 4/1991 |

(56) References Cited

FOREIGN PATENT DOCUMENTS

| | | |
|---|---|---|
| JP | 05-277154 | 10/1993 |
| JP | 11-071554 | 3/1999 |
| SE | 331736 | 1/1971 |
| WO | WO 84/02473 | 7/1984 |
| WO | WO 85/04813 | 11/1985 |
| WO | WO 86/01115 | 2/1986 |
| WO | WO 91/02484 | 3/1991 |
| WO | WO 92/15349 | 9/1992 |
| WO | WO 93/01845 | 2/1993 |
| WO | WO 95/35124 | 12/1995 |
| WO | 97/08054 | 3/1997 |
| WO | 98/27926 | 7/1998 |
| WO | 98/44043 | 10/1998 |
| WO | WO 99/06082 | 2/1999 |
| WO | 99/48990 | 9/1999 |
| WO | WO 01/91829 | 12/2001 |

OTHER PUBLICATIONS

U.S. Appl. No. 11/675,475, filed Feb. 15, 2007, Bedingfield.
Written Opinion of the International Searching Authority for International Application No. PCT/US2008/053796 dated Jul. 29, 2008.
Notification Concerning Transmittal of International Preliminary Report on Patentability for International Application No. PCT/US2008/053796 mailed on Aug. 27, 2009.
Opening Expert Witness Report of Dr. Juan Santiago Regarding Anticipation and Obviousness of the Claims of U.S. Patents Nos. 6,503,062 and 6,808,369 in view of the Prior Art and based on the Indefiniteness, Lack of Enablement, and Lack of Written Description of Certain Claims of U.S. Patent Nos. 6,503,062 and 6,808,369, Apr. 24, 2009.
Opening Expert Witness Report of William K. Durfee Regarding whether Certain Claims of U.S. Patent No. 5,324,422, U.S. Patent No. 5,421,823, U.S. Patent No. 5,431,626 and U.S. Patent No. 5,438,510 were Ready for Patenting, Apr. 24, 2009.
Expert Witness Report of Fred K. Forster: Analysis of Obviousness of Certain Asserted Claims of U.S. Patent Nos. 5,431,626; 5,324,422; and 5,438,510, Apr. 24, 2009.
Expert Witness Report of Ronald J. Adrian Regarding Lack of Written Description, Lack of Enablement, and Indefiniteness of the Asserted Claim (Claim 12) of U.S. Patent No. 6,814,547, Apr. 24, 2009.
Exhibit A, Credentials of Ronald J. Adrian.
Exhibit B, Materials Considered by Ronald J. Adrian.
Expert Report on Development of the PD700 and Motivation to Combine the PD700 and U.S. Patent No. 5,088,515, Sven Olofsson, Apr. 24, 2009.
Expert Witness Report of Juan G. Santiago Regarding Lack of Written Description, Non-Enablement, and Indefiniteness of the Asserted Claims of U.S. Patent Nos. 5,421,823; 5,324,422; 5,438,510; and 5,431,626, Apr. 24, 2009.
Opening Expert Witness Report of Dr. Martin Roberts Regarding a History of Peritoneal Dialysis and the Obviousness and Consequent Invalidity of the Asserted Claims of U.S. Patent No. 5,421,823, Apr. 24, 2009.
Opening Expert Witness Report of Dr. Darrell Long Regarding Technical Features of the High Flow Peritoneal Dialysis and Personal Cycler Machines, Apr. 24, 2009.
Defendants' Preliminary Invalidity Contentions for U.S. Patent No. 5,421,823, *Baxter Healthcare Corporation v. Fresenius Medical Care Holdings*, Case No. C 07-01359 PJH (JL), filed Aug. 24, 2007.
Defendants' Supplemental Invalidity Contentions for U.S. Patent No. 5,421,823, *Baxter Healthcare Corporation v. Fresenius Medical Care Holdings*, Case No. C 07-01359 PJH (JL), filed Jan. 31, 2008.
Defendants' Preliminary Invalidity Contentions for U.S. Patent No. 6,503,062, *Baxter Healthcare Corporation v. Fresenius Medical Care Holdings*, Case No. C 07-01359 PJH (JL), filed Jan. 31, 2008.
Defendants' Preliminary Invalidity Contentions for U.S. Patent No. 6,808,369, *Baxter Healthcare Corporation v. Fresenius Medical Care Holdings*, Case No. C 07-01359 PJH (JL), filed Jan. 31, 2008.
Defendants' Preliminary Invalidity Contentions for U.S. Patent No. 5,324,422, *Baxter Healthcare Corporation v. Fresenius Medical Care Holdings*, Case No. C 07-01359 PJH (JL), filed Jan. 31, 2008.
Defendants' Preliminary Invalidity Contentions for U.S. Patent No. 5,438,510, *Baxter Healthcare Corporation v. Fresenius Medical Care Holdings*, Case No. C 07-01359 PJH (JL), filed Jan. 31, 2008.
Defendants' Preliminary Invalidity Contentions for U.S. Patent No. 6,814,547, *Baxter Healthcare Corporation v. Fresenius Medical Care Holdings*, Case No. C 07-01359 PJH (JL), filed Jan. 31, 2008.
Defendants' Preliminary Invalidity Contentions for U.S. Patent No. 5,431,626, *Baxter Healthcare Corporation v. Fresenius Medical Care Holdings*, Case No. C 07-01359 PJH (JL), filed Jan. 31, 2008.
Defendants' Preliminary Invalidity Contentions for U.S. Patent No. 6,929,751, *Baxter Healthcare Corporation v. Fresenius Medical Care Holdings*, Case No. C 07-01359 PJH (JL), filed Jan. 31, 2008.
Defendants' Preliminary Invalidity Contentions for U.S. Patent No. 7,083,719, *Baxter Healthcare Corporation v. Fresenius Medical Care Holdings*, Case No. C 07-01359 PJH (JL1), filed Jan. 31, 2008.
Defendants' Final Invalidity Contentions for U.S. Patent No. 6,814,547, *Baxter Healthcare Corporation v. Fresenius Medical Care Holdings*, Case No. C 07-01359 PJH (JL), filed Apr. 1, 2009.
Fresenius 90/2 Peritoneal Therapy Cycler (on information and belief, on sale in United States by 1991).
Blumenkrantz et al., Applications of the Redy Sorbent System to Hemodialysis and Peritoneal Dialysis, Artificial Organs, vol. 3, No. 3 (Aug. 1979).
Blumenkrantz et al., Development of a Sorbent Peritoneal Dialysate Regeneration System—A Progress Report, European Dialysis and Transplant Association 1978.
Blumenkrantz and Roberts, Progress in Peritoneal Dialysis: a Historical Prospective, Contributions to Nephrology, vol. 17, pp. 101-110 (1979).
Diaz-Buxo, CCPD is even better than CAPD, Kidney International, vol. 28, Suppl. 17, pp. S-26-S-28 (1985).
Diaz-Buxo, CCPD Technique and Current Clinical Experience (1982).
Diaz-Buxo, et al., Continuous Cyclic Peritoneal Dialysis: A Preliminary Report, Artificial Organs, vol. 5, No. 2, pp. 157-161 (May 1981).
Diaz-Buxo, Current Status of Continuous Cyclic Peritoneal Dialysis (CCPD), Peritoneal Dialysis International, vol. 9, pp. 9-14 (1989).
Diaz-Buxo, Issues in Nephrology: Continuous Cyclic Peritoneal Dialysis, NAPHT News, Feb. 1983, pp. 12-14.
Diaz-Buxo, Peritoneal Dialysis Reverse Osmosis Machines and Cyclers, Dialysis Therapy, pp. 41-48 (1986).
Drukker et al., Replacement of Renal Function by Dialysis, 2nd Ed., Ch. 21, 1983.
Lewin and Maxwell, Sorbent-Based Regenerating Peritoneal Dialysis, Sorbents and Their Clinical Applications, pp. 353-374 (1980).
Lewin et al., Sorbent for Application in the Treatment of ESRD Patients, Annual Progress Report re Contract #N01-AM-9-2215, submitted Jun. 22, 1982.
Ratnu, et al., A New Technique—Semicontinuous Rapid Flow, High Volume Exchange—For Effective Peritoneal Dialysis in Shorter Periods, Nephron, vol. 31, pp. 159-163 (1982).
Twardowski, Peritoneal Dialysis: Current Technology and techniques, Postgraduate Medicine, vol. 85, No. 5 (Apr. 1989).
Product Evaluation Reports: Peritoneal Dialysis Machine "Pac-X," Hospital Materials Management, vol. 12, No. 11, p. 16 (Nov. 1987).
Brochure entitled, AP Hauni: Automatisches Peritonealdialyse-Great (1970).
Brochure entitled, Fresenius Delivers 90/2 Peritoneal Therapy Cycler.
Brochure entitled, REDY Universal Re-circulating Dialysate System.
Brochure entitled, SIF 901 Perugia.
Translation of brochure entitled, SIF 901 Perugia.
Translation of Certificate for translation of brochure entitled, SIF 901 Perugia.
Operators Instructions for Fresenius 90/2 Peritoneal Therapy Cycler.
Photo of dialysis patient connected to machine.
Photo of dialysis machine.
Peritoneal Dialyser PD700 Service Manual, Jun. 1977.
Peritoneal Dialyser PD700 Instruction Manual.

(56) References Cited

OTHER PUBLICATIONS

PD700 Peritoneal Dialyser Users Hand-book, Dec. 1977.
Operating Instructions, Peritoneal Dialyser PD700, For Ser. No. 300.
Brochure entitled, Peritoneal Dialyser PD700, May 1979.
Brochure entitled, For Volume Measurement, Temperature Control and Cycling of Dialysing Fluid, Peritoneal Dialyser PD700, 1970.
Skotselanvisning for Peritoneal—Dialysapparat PD700.
Bergstrom et al., An Automated Apparatus for Peritoneal Dialysis with Volumetric Fluid Balance Measurement, reprinted from Dialysis & Transplantation, Jun./Jul. 1976.
U. Callsen, Peritoneal-Dialysator PD700, Prakt. Anasth. 9 (1974).
Piazolo et al., Erfahrungen mit einem neuen vollautomatsischen Paritoneal-dialysegerat, Munchener Medizinische Wochenschrift, 1972.
Technical Note, PD700 Peritoneal Dialyser, Jan. 29, 1979.
Assorted Photos of dialysis machine with and without casing on.
Elsevier Science Ltd., Air-Operated Diaphragm Pumps, World Pumps, Jan. 1996, at 38.
Bran & Luebbe GmbH, Diaphragm Metering Pumps, Chem. Eng'g Progress, Apr. 1987, at 18-24.
M. Schalbach, E.S. Bucherl & O. Franke, An Electronically Controlled Implantable Auxiliary Ventricle, published in Advances in Biomedical Engineering and Medical Physics: Cardiac Engineering, vol. 3.
Gene L. Mrava, Mock Circulation Systems for Artificial Hearts, published in Advances in Biomedical Engineering and Medical Physics: Cardiac Engineering, vol. 3.
W.M. Phillips, J.A. Brighton & W.S. Pierce, Artificial Heart Evaluation Using Flow Visualization Techniques, published in Transactions: American Society for Artificial Internal Organs, vol. XVIII (1972).
J.A. Brighton, W.S. Pierce, D.Landis & G. Rosenberg, Measuring Cardiac Output of Pneumatically Driven Total Artificial Hearts, published in 30th Anniversary Conference on Engineering in Medicine and Biology: Proceedings, vol. 19 (Nov. 5-9, 1977).
Operator's Instructions, Fresenius 90/2 Peritoneal Therapy Cycler (Rev. C. copyright 1991-2000).
Memorandum of Donald X. Vaccarino entitled 90/2 History File (1991-1992).
Document entitled 90/2 Cycler Software, Version 3.96 (Jan. 24, 1992).
Software Change Requests (Jul. 8, 1991-Oct. 3, 1992).
Brochure entitled Fresenius Delivers 90/2 Peritoneal Therapy Cycler (Apr. 2001).
90/2 Quick Reference.
90/2 Cycler Parts List (Nov. 6, 1997).
90/2 Cycler Box Contents.
90/2 Brochure (Jul. 1993).
90/2 Brochure (Apr. 2001).
90/2 Directions for Use.
90/2 Document Index.
Freedom Cycler Document Index.
Specification entitled Inpersol Cycler 3000 Operating Manual, List No. 21952-04, dated 1990.
Training aid entitled Learning to Use the Inpersol Cycler 3000, dated Jul. 1991.
Fresenius USA/Delmed 90/2 Peritoneal Dialysis System Operators Manual, dated Feb. 6, 1991.
Fresenius 90/2 Peritoneal Therapy Cycler Operator's Instructions, dated 2000.
Fresenius 90/2 PD Cycler Set Patient Information Card.
Fresenius Freedom Cycler Operating Instructions.
Exhibit A, Credentials of Ronald J. Adrian, Apr. 24, 2009.
Exhibit B, Materials Considered by Ronald J. Adrian, Apr. 24, 2009.
Brochure entitled, REDY Universal Re-circulating Dialysate System, 1980.
Brochure entitled Fresenius Delivers 90/2 Peritoneal Therapy Cycler, Apr. 2001.
Schalbach, Bucherl & Franke, An Electronically Controlled Implantable Auxiliary Ventricle, published in Advances in Biomedical Engineering and Medical Physics: Cardiac Engineering, vol. 3 (Apr. 11, 1974).
Mrava, Gene, L, Mock Circulation Systems for Artificial Hearts, published in Advances in Biomedical Engineering and Medical Physics: Cardiac Engineering, vol. 3, 1970.
Operating Instructions, Peritoneal Dialyser PD700, For Serial No. 300, 1979.

* cited by examiner

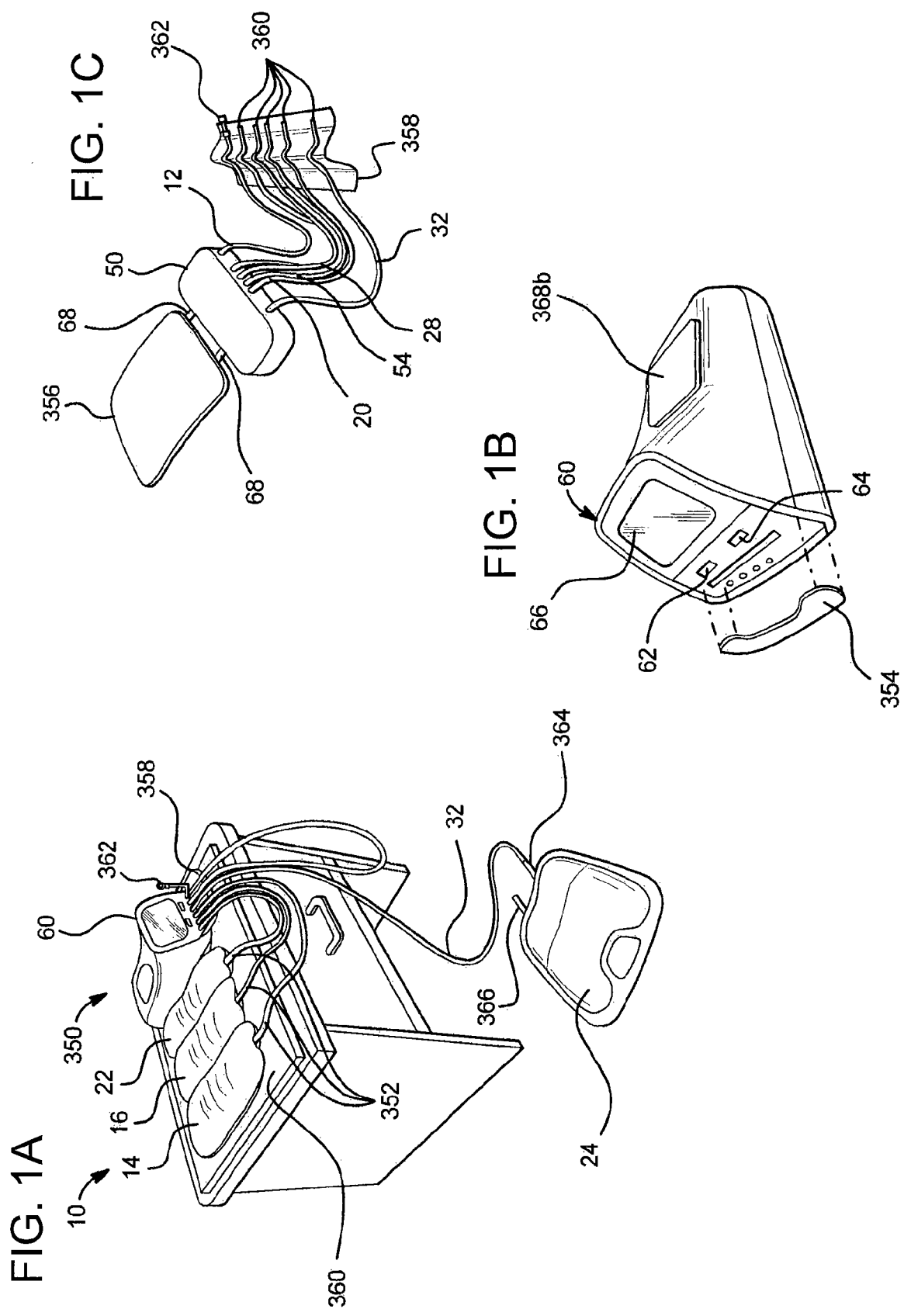

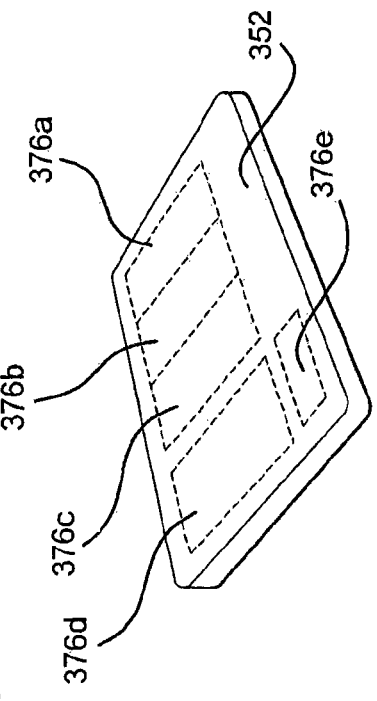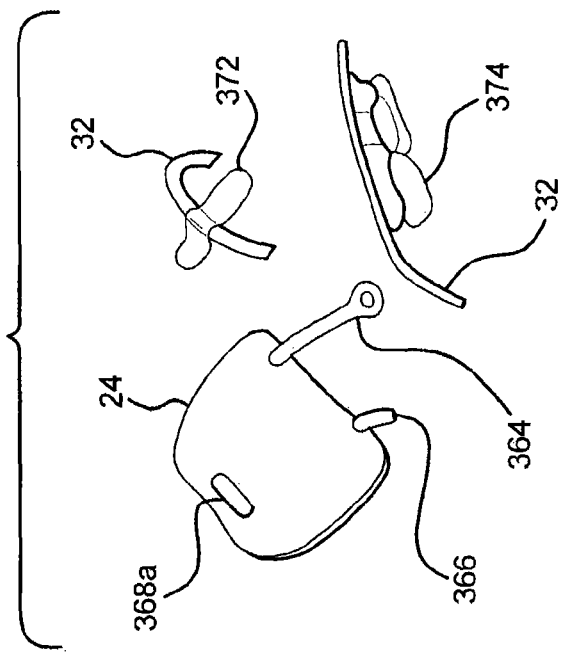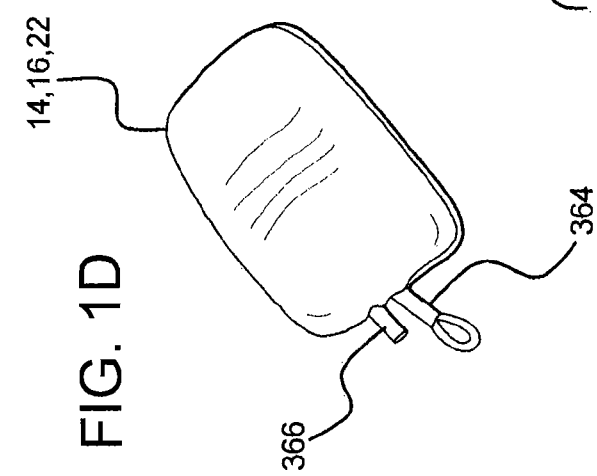

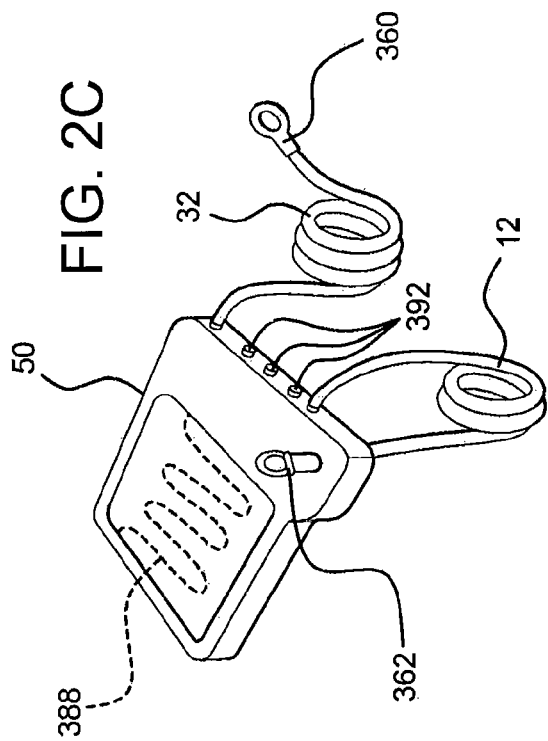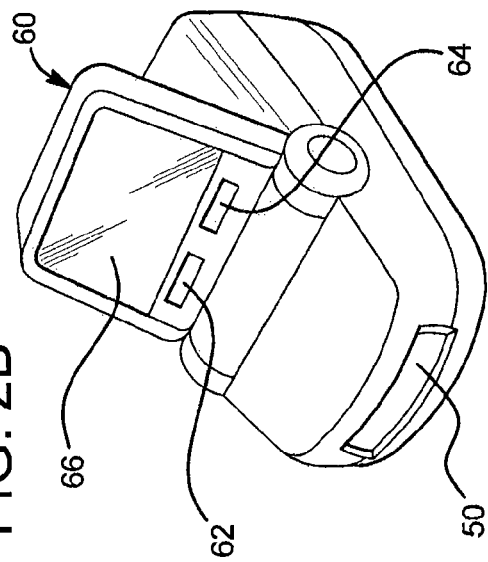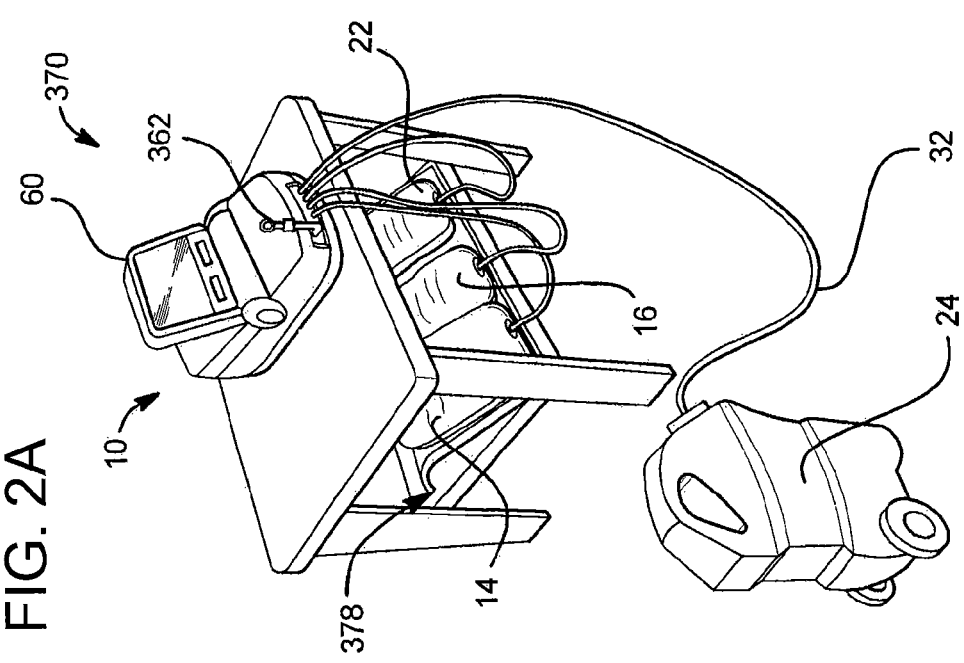

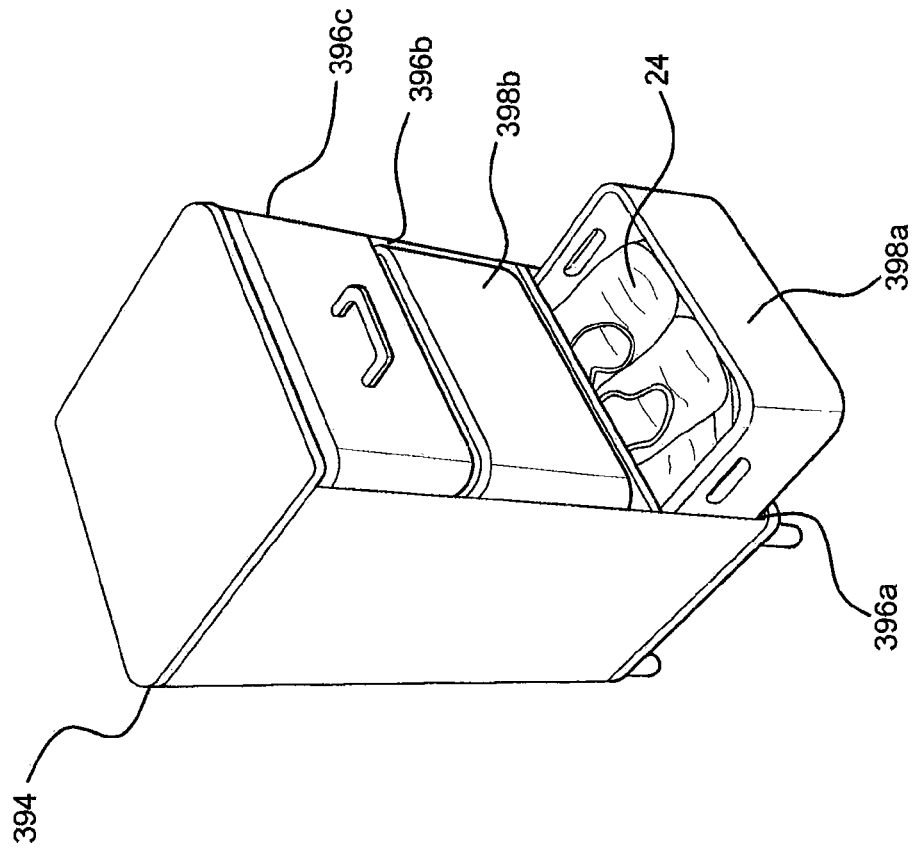
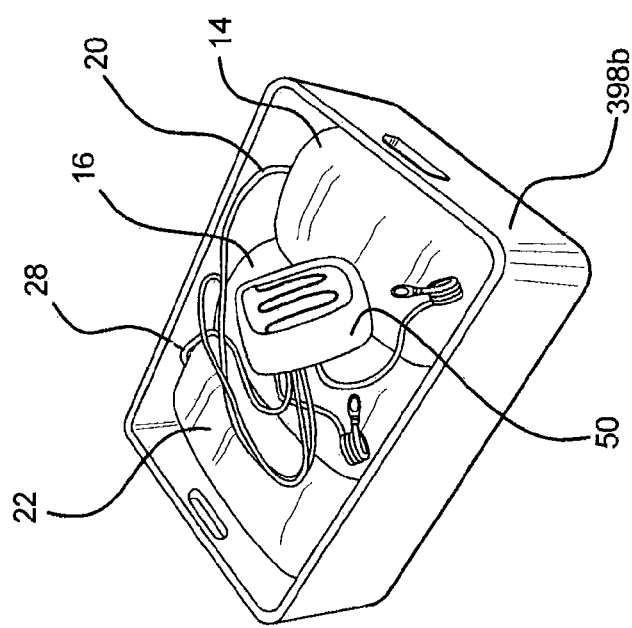

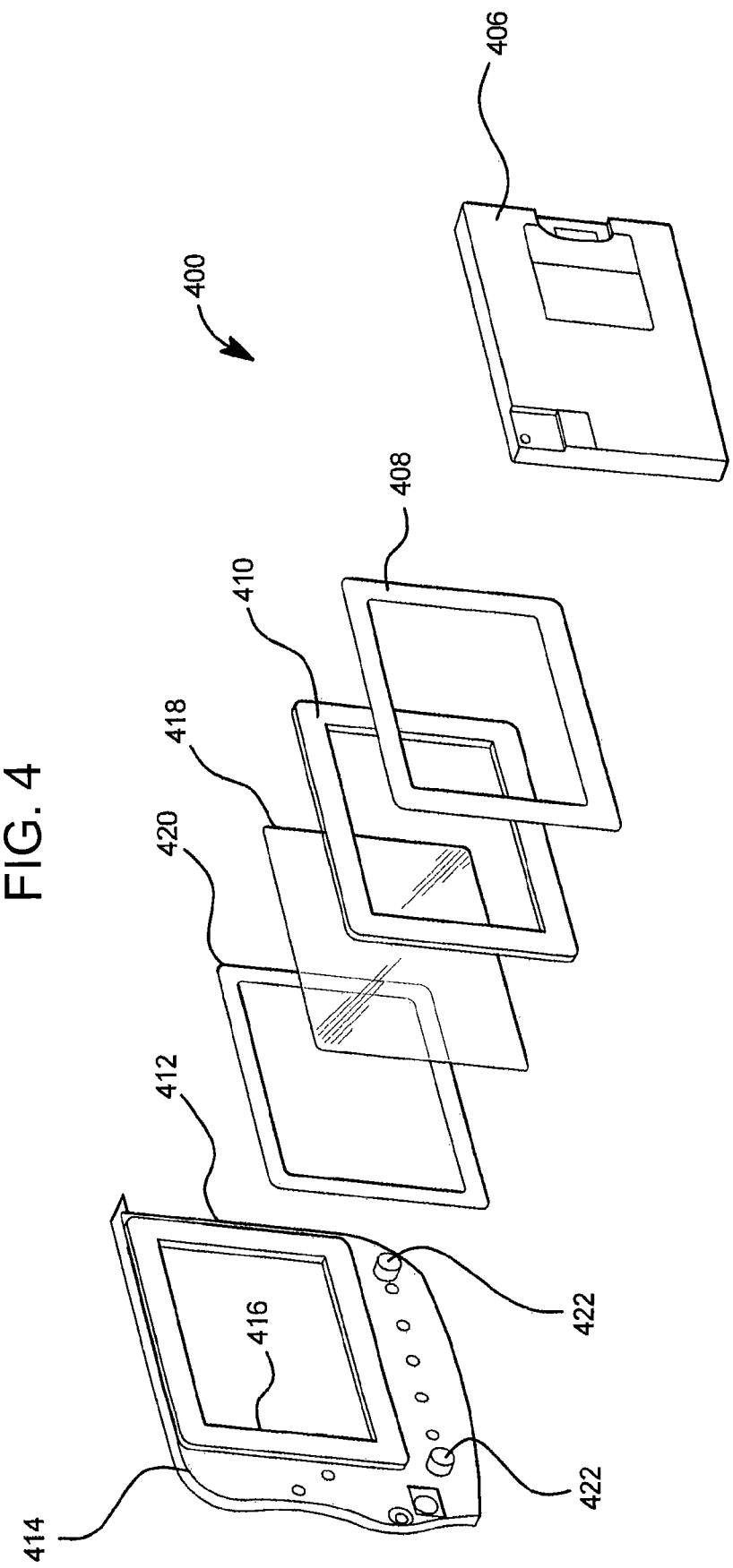

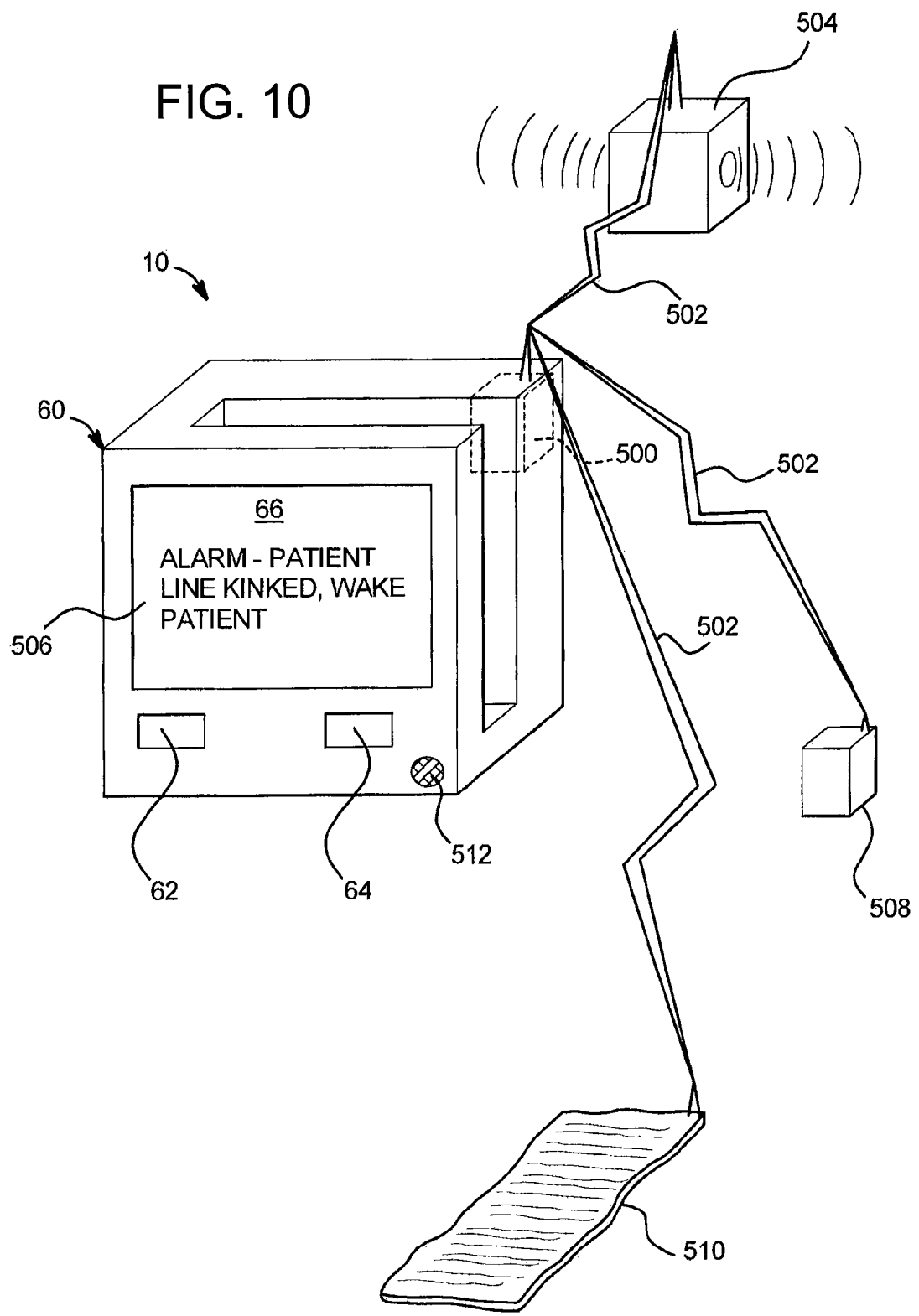

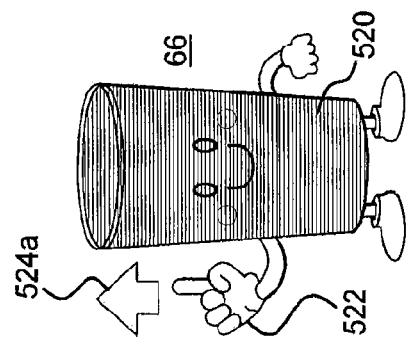
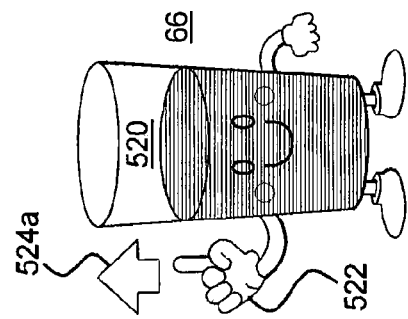
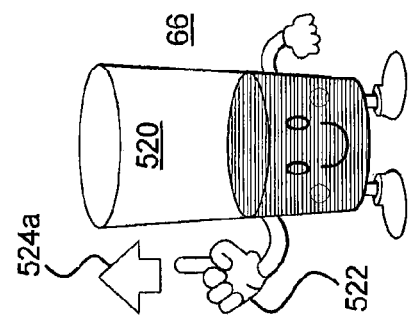
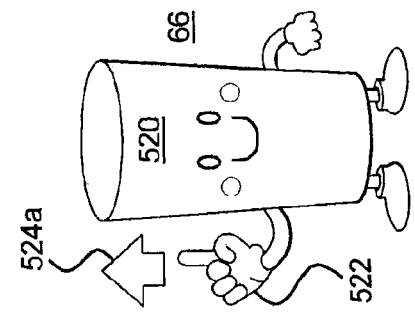

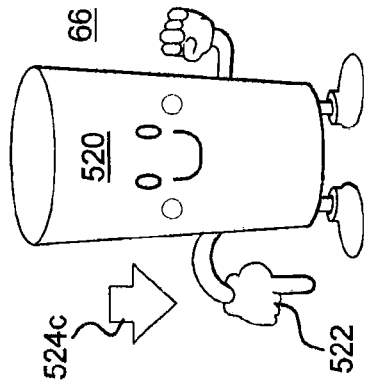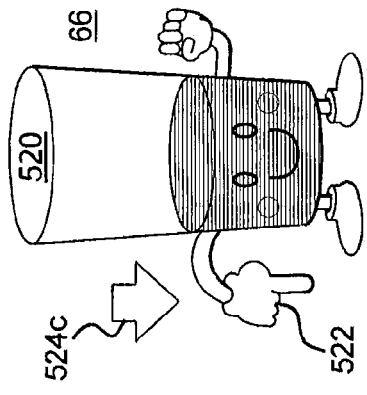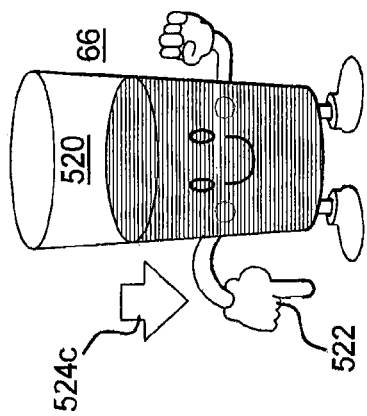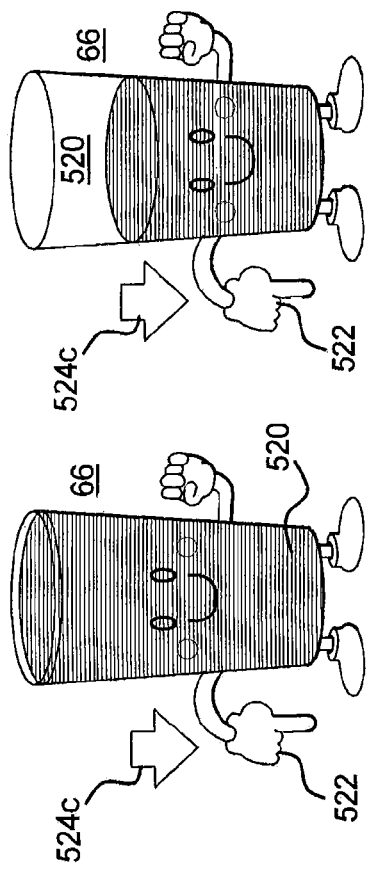

DIALYSIS SYSTEM HAVING VIDEO DISPLAY WITH AMBIENT LIGHT ADJUSTMENT

BACKGROUND

In general, the present disclosure relates to medical fluid delivery systems that employ a pumping cassette. In particular, the present disclosure provides systems, methods and apparatuses for cassette-based dialysis medical fluid therapies, including but not limited to those using peristaltic pumps and diaphragm pumps.

Due to various causes, a person's renal system can fail. Renal failure produces several physiological derangements. The balance of water, minerals and the excretion of daily metabolic load is no longer possible and toxic end products of nitrogen metabolism (urea, creatinine, uric acid and others) can accumulate in blood and tissue.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life-saving.

Hemodialysis and peritoneal dialysis are two types of dialysis therapies used commonly to treat loss of kidney function. Hemodialysis treatment utilizes the patient's blood to remove waste, toxins and excess water from the patient. The patient is connected to a hemodialysis machine and the patient's blood is pumped through the machine. Catheters are inserted into the patient's veins and arteries so that blood can flow to and from the hemodialysis machine. The blood passes through a dialyzer of the machine, which removes waste, toxins and excess water from the blood. The cleaned blood is returned to the patient. A large amount of dialysate, for example about 120 liters, is consumed to dialyze the blood during a single hemodialysis therapy. Hemodialysis treatment lasts several hours and is generally performed in a treatment center about three or four times per week.

Peritoneal dialysis uses a dialysis solution, or "dialysate," which is infused into a patient's peritoneal cavity via a catheter. The dialysate contacts the peritoneal membrane of the peritoneal cavity. Waste, toxins and excess water pass from the patient's bloodstream, through the peritoneal membrane and into the dialysate due to diffusion and osmosis, i.e., an osmotic gradient occurs across the membrane. The spent dialysate is drained from the patient, removing waste, toxins and excess water from the patient. This cycle is repeated.

There are various types of peritoneal dialysis therapies, including continuous ambulatory peritoneal dialysis ("CAPD"), automated peritoneal dialysis ("APD"), tidal flow APD and continuous flow peritoneal dialysis ("CFPD"). CAPD is a manual dialysis treatment. The patient manually connects an implanted catheter to a drain, allowing spent dialysate fluid to drain from the peritoneal cavity. The patient then connects the catheter to a bag of fresh dialysate, infusing fresh dialysate through the catheter and into the patient. The patient disconnects the catheter from the fresh dialysate bag and allows the dialysate to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement.

Automated peritoneal dialysis ("APD") is similar to CAPD in that the dialysis treatment includes drain, fill, and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysate and to a fluid drain. APD machines pump fresh dialysate from a dialysate source, through the catheter, into the patient's peritoneal cavity, and allow the dialysate to dwell within the cavity, and allow the transfer of waste, toxins and excess water to take place. The source can be multiple sterile dialysate solution bags.

APD machines pump spent dialysate from the peritoneal cavity, though the catheter, to the drain. As with the manual process, several drain, fill and dwell cycles occur during APD. A "last fill" occurs at the end of CAPD and APD, which remains in the peritoneal cavity of the patient until the next treatment.

Both CAPD and APD are batch type systems that send spent dialysis fluid to a drain. Tidal flow systems are modified batch systems. With tidal flow, instead of removing all of the fluid from the patient over a longer period of time, a portion of the fluid is removed and replaced after smaller increments of time.

Continuous flow, or CFPD, systems clean or regenerate spent dialysate instead of discarding it. The systems pump fluid into and out of the patient, through a loop. Dialysate flows into the peritoneal cavity through one catheter lumen and out another catheter lumen. The fluid exiting the patient passes through a reconstitution device that removes waste from the dialysate, e.g., via a urea removal column that employs urease to enzymatically convert urea into ammonia. The ammonia is then removed from the dialysate by adsorption prior to reintroduction of the dialysate into the peritoneal cavity. Additional sensors are employed to monitor the removal of ammonia. CFPD systems are typically more complicated than batch systems.

Hemodialysis, APD (including tidal flow) and CFPD systems can employ a pumping cassette. The pumping cassette typically includes a flexible membrane that is moved mechanically to push and pull dialysis fluid out of and into, respectively, the cassette. Certain known systems include flexible sheeting on one side of the cassette, while others include sheeting on both sides of the cassette. Positive and/or negative pressure can be used to operate the pumping cassettes.

As described herein, the present disclosure provides a number of improvements to such fluid delivery systems.

SUMMARY

A first aspect of the embodiments described herein includes improved product configurations. Here, different parts of the cassette-based peritoneal dialysis system are configured advantageously, such as: (i) operational placement of the system; (ii) user interface configuration and orientation; (iii) disposable cassette loading; (iv) cassette/heater and bag/tube management; (v) solution bag configuration; (vi) drain bag configuration; and (vii) storage and supply organization.

An second aspect of the embodiments described herein includes a capacitance electromagnetic compliance ("EMC") seal for the display of the user interface of the dialysis system. The seal as seen below does not cover the viewable portion of the display, improving light transmittance and image quality versus known seals.

A third aspect of the embodiments described herein includes an elastomeric keypad for use with the display of the user interface of the dialysis system. The keypad, among other features, includes an ambient light sensor that provides a signal output, which is used to control adjustment of display brightness and contrast based on a change in ambient light.

A fourth aspect of the embodiments described herein includes a low battery disconnect circuit for the dialysis system. The circuit allows the battery back-up disconnect voltage to be set closer to the regulated voltage, enabling the dialysis system to operate longer on battery back-up power.

A fifth aspect of the embodiments described herein includes an improved silent alarm for the dialysis system. The silent alarm system, among other features, includes a transmitter that sends a signal to a remote alarming device, which can alert a caregiver to a dialysis system failure without disturbing the patent and/or people around the patent, who may be sleeping.

A sixth aspect of the embodiments described herein includes a visual symbol or character shown on the display of the user interface of the dialysis system, which communicates pictorially ongoing happenings of the therapy, such as: (i) patient fill; (ii) solution dwell; (iii) patient drain; (iv) therapy status; (v) alarm status; (vi) patient history; (vii) therapy completed successfully; and (viii) system shut down.

A first primary embodiment includes improved product configurations. Here, the cassette-based dialysis system can be configured to be placed on a patient's existing nightstand or be provided with its own nightstand. The instrument or actuator unit of the system can be configured to accept the disposable cassette horizontally or vertically. The display and user interface of the actuator unit may be integral to the actuator unit and for example be mounted at an upright angle or be rotatable and closeable with respect to the remainder of the actuator unit.

It is also contemplated to arrange the disposable cassette, heater bag, supply bag and tubing in a variety of advantages configurations. In one implementation the disposable cassette is integrated to the heater bag. In another implementation, the heater bag is coupled to ports extending from the disposable cassette. The solution bags may be configured with any one or more of: (i) a spike seal that ensures a solution bag seal prior to pinching the solution bag; (ii) pre-attached tubing; and/or (iii) a delivery tray. The tubing may be configured with any one or more of: (i) the supply tubes tacked together; (ii) a larger diameter draw hose; (iii) the patient and/or drain line coiled; (iv) the patient and/or drain lines pre-attached to the cassette; (v) leur connections provided on the supply tubes for ready attachment to the supply bags; (vi) the patient tube pre-attached to the disposable cassette so as to be in proper orientation for operation with a primary sensor; (vii) clamps color-coded and/or configured with line identification.

The drainage for the dialysis system may also be configured advantageously in a variety of ways. For example the drain tubes may be provided with adhesive bonding and/or a clamp to help secure the drain bag and/or the drain bag. The drain bag may be configured: (i) with a handle; (ii) to be reusable; (iii) to be a flexible bag or an at least semi-rigid container; (iv) to be a container with a handle oriented to easily tip the container and/or with wheels; and (v) to be pre-attached to the drain tube and/or the disposable cassette.

The organization of the dialysis system is also configurable in a variety of ways advantageously. One implementation includes an organizational mat that prompts the patient to organize the fluid bags/containers properly and to gather the supplies needed. Another implementation provides a solution bag tray that orients the solution bags for optimum performance. Still a further implementation provides a nightstand, which holds any one or more of: (i) the actuator unit; (ii) additional supplies; (iii) solution/drain bag; (vi) disposable cassette; and (v) tubing.

A second primary embodiment includes an improved display device, which employs a capacitance electromagnetic compliance ("EMC") seal. The display device includes an insulating dielectric material (e.g., mylar film) placed between the metal case of the display device or monitor and a conductive coating located on the housing of the dialysis machine. The metal case and metal coating are electrically isolated from each other. The dielectric material and the two conductive surfaces form a capacitor that prevents leakage of electromagnetic energy.

A third primary embodiment includes an improved elastomeric keypad. The keypad, among other features, includes an ambient light sensor that provides a signal output that the dialysis system uses to adjust the brightness and contrast of the display based on the amount of ambient light sensed. The ambient light sensor is imbedded into or is otherwise secured by the machine housing such that at least a portion of the sensor is oriented to be able to gather ambient light. The sensor is connected with electronics to a backlight control function. The output of the backlight control function controls the brightness of the user interface display and keyboard backlighting. In one implementation, an increase in ambient light results in a corresponding increase in backlight intensity. Conversely, a decrease in ambient light results in a corresponding decrease in backlight intensity.

In one implementation, a medical therapy machine includes: an enclosure; a medical therapy machine component located inside the enclosure; a video monitor supported by the enclosure and displaying at least one of information and indicia relating to the medical therapy; an ambient light sensor positioned with respect to the enclosure so as to be able to sense a level of ambient light impinging the enclosure; and a logic implementor configured to control a level of backlight brightness for the video monitor based on the level of ambient light sensed by the sensor.

In one implementation, the sensor includes a photoreceptor having a spectral response approximating that of a human eye.

In one implementation, the logic implementor includes at least one of: a dedicated analog circuit, a dedicated digital circuit, a microcontroller, a hybrid circuit and microcontroller and a functional element of a shared applications processor.

In one implementation, the machine includes interface circuitry configured to interface an output of the sensor with the logic implementor.

In one implementation, the machine includes a manual brightness input device coupled operably to the logic implementor, the implementor and input device configured to enable a user of the machine to set an initial level of backlight brightness.

In one implementation, the logic implementor is configured to do at least one of: (i) increase the level of backlight brightness for the video monitor when the sensor senses an increased level of ambient light; and (ii) decrease the level of backlight brightness for the video monitor when the sensor senses a decreased level of ambient light.

In one implementation, the video monitor is operable with a touch screen.

In one implementation, the video monitor and the touch screen are configured to provide at least one selectable input for controlling a parameter relating to the medical therapy, the logic implementor configured to control the level of backlight brightness for the at least one selectable input individually based on the level of ambient light sensed by the sensor.

In one implementation, the machine includes a keypad operable with the video monitor, the logic implementor configured to control the level of backlight brightness for the keypad based on the level of ambient light sensed by the sensor.

In one implementation, the keypad includes a plurality of selectable buttons for controlling a parameter relating to the medical therapy, the logic implementor configured to selectively and individually backlight at least one of the buttons.

In one implementation, the keypad includes a plurality of buttons, the display configured to show indicia relating to one of the buttons, the logic implementor configured to backlight the button while the indicia is shown on the video monitor.

In one implementation, a medical therapy machine includes: an enclosure; a medical therapy machine component located inside the enclosure; a video display supported by the enclosure and displaying at least one of information and indicia relating to the medical therapy; an ambient light sensor positioned with respect to the enclosure so as to be able to sense a level of ambient light impinging the enclosure; and a logic implementor configured to control a level of backlight brightness for the video display based on the level of ambient light sensed by the sensor.

In one implementation, at least one of the buttons includes at least one characteristic selected from the group consisting of: (i) having a three dimensional shape; (ii) being raised; (iii) having an associated unique icon inset from a surface of the button; (iv) being color-coded; (v) being individually capable of being backlit; (vi) being hidden and locatable via identifying markings on the keypad; (vii) being configured to provide tactile feedback when pressed; and (viii) being configured as at least one of an up and down parameter adjuster.

In one implementation, the logic implementor is further configured to control the level of backlight brightness based on a person's natural night vision adjustment.

In one implementation, a medical therapy machine includes: an enclosure; a medical therapy machine component located inside the enclosure; a video display supported by the enclosure and displaying at least one of information and indicia relating to the medical therapy; a keypad operable with the video display, the keypad including a plurality of buttons; and a logic implementor configured to increase a level of backlight brightness for at least one of: (i) the display; and (ii) at least one of the buttons when a level of ambient light impinging on the enclosure increases.

In one implementation, the display is configured to show indicia relating to one of the buttons, the logic implementor configured to backlight the button while the indicia is shown on the display.

A fourth primary embodiment includes a low battery disconnect circuit for use with the peritoneal dialysis machine. The cassette-based system includes a battery back-up power source. When the system is obtaining power from the battery back-up, the output voltage of the battery back-up gradually declines over time. The battery output is connected to a voltage regulator circuit that regulates the battery output to a constant level. As the battery voltage declines, a point can be reached in which the regulator can no longer hold the output voltage constant. The disconnect circuit serves to optimize this point to increase the life of the battery back-up power source.

The regulator circuit includes a metal oxide field effect transistor ("MOSFET"). In the circuit, the MOSFET acts as a variable resistor according to its inherent on-resistance versus gate voltage characteristic. The regulator controller compares a feedback voltage at the source of the MOSFET to an internal voltage reference and adjusts the voltage at the gate of the MOSFET to produce a desired, regulated output voltage. As the battery voltage declines, the regulator controller increases the voltage at the gate of the MOSFET, which according to the on-resistance versus gate voltage characteristic decreases the drain to source resistance, reducing the voltage drop across the MOSFET, so as to maintain the MOSFET source pin at a desired regulated voltage. As described in detail below, the MOSFET regulator controller and the remainder of the circuit enable the disconnection of the battery to be made at a voltage very close to the regulated voltage, maximizing battery back-up time. The circuit prolongs the use of the battery back-up and enables more cost effective components to be used.

A fifth primary embodiment includes a silent or remote alarm apparatus that operates with the cassette-based peritoneal dialysis system. The system contains speakers that can be used to sound audible alarms at the machines. The system also includes a transmitter that can be used alternatively to send a signal to a remote alerting device. The display of the machine shows a visual message detailing the type of the alarm and/or instructions for addressing the alarm. A receiving unit receives a signal sent by the transmitter and generates an audio, visual and/or physical (e.g., vibrating) alarming output to the patient or to a caregiver or hospital member located remotely with respect to the patient. The signal for example can be sent to a bed shaker that wakes only the person that needs to be awakened, e.g., the patient or caregiver. Family members or other patients in the room with the patient do not have to be awakened needlessly.

In an sixth primary embodiment, the user interface displays a figure or character that shows the progress of a number of treatment steps for the dialysis treatment. In the embodiments illustrated herein, the display of the user interface displays a cartoon, video or other changeable image of a drinking glass. The glass is filled during fill, dwell and drain cycles. The filling of the glass in essence tracks the time or percentage of completeness of the particular cycle. The glass includes indicia indicating whether the cycle is a fill, dwell or drain cycle.

The glass is non-imposing and provides a friendlier way to instruct the patient during therapy. The glass is incorporated into other aspects of peritoneal dialysis, such as alarm conditions, status reports, patient history, therapy completed successfully and system shut down.

It is therefore an advantage of the embodiments described herein is to provide improved configurations for the components of a cassette-based dialysis system.

Another advantage of the embodiments described herein to provide improvements to the user interface of the dialysis system, such as an improved display, an improved keypad, an improved alarming capability and an improved state of therapy and therapy feature indication.

Yet a further advantage of the embodiments described herein is to provide an improved battery back-up feature for a cassette-based dialysis system.

Additional features and advantages of the embodiments described herein are described in, and will be apparent from, the following Detailed Description of the Disclosure and the figures.

BRIEF DESCRIPTION OF THE FIGURES

FIGS. 1A to 1F are perspective views illustrating different components of one configuration of a dialysis system employing the embodiments discussed herein.

FIGS. 2A to 2F are perspective views illustrating different components of another configuration of a dialysis system employing the embodiments discussed herein.

FIGS. 3A to 3E are perspective views illustrating different components of a further configuration of a dialysis system employing the embodiments discussed herein.

FIG. 4 is a perspective view illustrating one example of a user interface for the dialysis system having a capacitance electromagnetic compliance ("EMC") seal.

FIG. 10 is a schematic view illustrating one example of a dialysis system employing the embodiments discussed herein having a silent alarm capability.

FIGS. 11A to 11D are machine screenshots illustrating an embodiment of a graphical depiction of a fill cycle of a dialysis system employing the embodiments discussed herein.

FIGS. 13A to 13D are machine screenshots illustrating an embodiment of a graphical depiction of a drain cycle of a dialysis system employing the embodiments discussed herein.

DETAILED DESCRIPTION

Figure 2F:
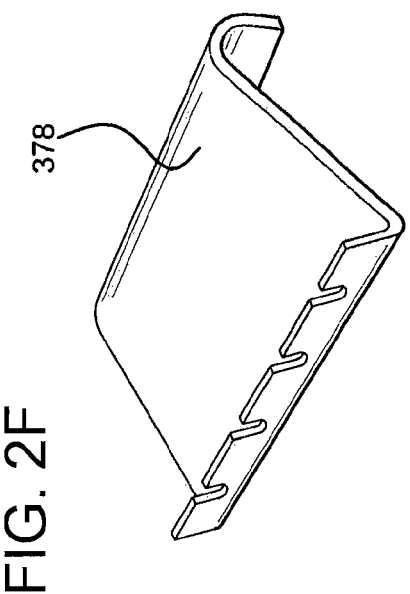

The embodiments described herein relate to medical fluid delivery systems that employ a pump, such as a peristaltic pump. In particular, systems, methods and apparatuses for cassette-based dialysis therapies including but not limited to hemodialysis, hemofiltration, hemodiafiltration, any type of continuous renal replacement therapy ("CRRT"), congestive heart failure treatment, CAPD, APD (including tidal modalities) and CFPD are disclosed. The cassette is disposable and typically discarded after a single use or therapy, reducing risks associated with contamination.

Product Configurations

Referring now to FIGS. 1A to 1F a first configuration for the components of system 10 is illustrated by configuration 350. As discussed herein, in one embodiment the pumping technology used for system 10 is a peristaltic pump. It is expressly contemplated, however, that many features and embodiments discusses herein can be used with peristaltic pumps, volumetric pumps, pumps operated pneumatically, pumps operated mechanically, pumps operated hydraulically and any combination thereof. The component features discussed in connection configuration 350 and indeed in connection with configurations 370 and 390 shown in connection with FIGS. 2A to 2F and 3A to 3F, respectfully, are applicable to any of the different types of pumping technologies just previously described. Indeed, while cassette 50 is shown in connection with each of configuration 350, 370 and 390.

As seen in FIG. 1A, configuration 350 of system 10 includes supply bags, 14, 16, and 22 and drain bag 24. Those bags are connected fluidly to machine or unit 60 via lines 28, 54, 20 and 32, respectfully, as seen in FIG. 1C additionally. FIG. 1A further illustrates that configuration 350 of system 10 includes an organizational mat 352, which is shown and discussed in more detail in connection with FIG. 1F. FIG. 1A further illustrates that configuration 350 can be placed partly on a desk or nightstand, with drain bag 24 being placed on the floor. In the illustrated embodiment, supply bags 14, 16 and 22 and cassette 50 are loaded and maintained in an at least substantially horizontal configuration.

Referring now to FIG. 1B, machine or unit 60 is illustrated in more detail. Here, unit 60 is a single integrated device, which includes a horizontal front drawer 354, the back of which curves vertically, so that a portion of cassette 50 is turned vertically for air separation purposes. Cassette 50 and heater bag 356, shown in more detail in connection with FIG. 1C, are loaded via drawer 354 simultaneously into unit 60. Drawer 354 also aids in organizing cassette 50 and beater bag 356 to aid the patient in aligning, inserting and removing those items. To that end, the identification of the separate lines 28, 54, 20 and 32 is also shown on drawer 354, so that the patient can match corresponding indicia on the lines with the markings on drawer 354 for proper cassette installation. In the illustrated embodiment, display 66 of machine or unit 60 is tilted at an angle of about forty-five degrees to about sixty degrees from vertical for ready viewing. Other angles could also be used. Unit 60 also includes controls 62 and 64, which can be off-screen controls, such as membrane switches, or on-screen controls, such as a touch screen overlay.

Referring now to FIG. 1C, the disposable, sterile, fluid carrying portion of configuration 350 is illustrated. The disposable set includes cassette 50 and separate heater bag 356, which are connected together via heater tubes. Thus, in configuration 350, heater 38 is located inside machine 60. As discussed above, unit 60 cooperates with drawer 354 to turn a portion of heater bag 356 upwards for air separation. In the illustrated embodiment, heater bag 356 is loaded first via drawer 354 into unit 60. The distill or free end of heater bag 356 is turned upward. That end may contain a vent or a filter, such as a hydrophobic membrane, which enables air escaping from the fluid in the heating pathway to collect at the vertical upper end of heater bag 356 and to eventually be vented through such a vent or filter.

The disposable set includes a tubing organizer 358, which can be placed on the table or night stand to further assist the loading of cassette 50 and heater bag 356. Organizer 358 holds supply lines 28, 54 and 20 next to one another. Those lines in an embodiment are tacked or otherwise held together, so that the patient knows that those lines are intended to be connected to supply bags 22, 16 and 14, respectively. Drain line 32 in an embodiment has a larger diameter hose than do supply lines 28, 54 and 20. This also helps the patient to keep the different lines straight in memory. Thus it should be appreciated that in configuration 350, cassette 50 and the lines connected to organizer 358 are loaded through the front of the unit 60, which places the tubes in an advantageous viewing area in front of the patient.

The identification of supply lines 28, 54 and 20, drain line 32 and patient line 12 is further aided via identifying markings. For example, clamps 360 (FIG. 1C) located at the distil ends of supply lines 20, 54, and 28 and drain line 32 are color-coded. Furthermore, the clamps can have molded line identification or indicia. Patient line 12 is identified via a connector 362 at its distil end. Connector 362 is removeably fixed to unit 60 as seen in FIG. 1A for priming. Unit 60 in one embodiment has a sensor, which senses whether connector 362 of patient line 12 is in proper position for priming before allowing therapy to begin.

As seen in FIG. 1D, supply bags 14, 16 and 22 each include a port 364 and a vent 366. Vent 366 for example includes a filter or a membrane, such as a hydrophobic membrane, which enables gas to be purged from the supply bags. Ports 364 each include a seal, which is spiked via the ends of supply lines 28, 54 and 20. The seal eliminates the need for a clamp on supply bag port 364.

Referring now to FIG. 1E, an embodiment for drain bag 24 is illustrated. Drain bag 24 also includes a port 364 and vent 366 as described above in connection with FIG. 1D. Bag 24 also includes a handle 368a, which aids in carrying bag 24 when it is full of spent fluid. A handle 368b is also provided with machine 60 as seen in connection with FIG. 1B for its ready transport. As seen in FIG. 1E, drain line 32 is provided with one or more apparatus, which enables the drain line to be fixed and held in a desired position. For example, drain line 32 can be provided with a flexible, adhesive-backed strip 372, which may enables the drain line to be adhered to the desk or night stand, for example. Strip 372 in an embodiment slidably engages drain line 372 in frictional manner, so that strip 372 can be moved along drain line 32 to a desirable position. Additionally or alternatively, a clamp 374, which can be reusable, is provided so that drain line 32 can be clamped in a desirable position. Clamp 374 slides over drain line 32 and in embodiment can be positioned frictionally along different areas of the drain line.

As seen in FIG. 1F, organizational mat 352 includes indicia 376a to 376e, which identifies the component at the illustrated location and where a component, such as the supply bag and drain bag, should be located. Mat 352 is reusable and made of a washable material. The indicia can further include written instructions, reminders and other useful information, such as color codes for the clamps and lines.

Referring now to FIGS. 2A to 2F, a second configuration 370 for system 10 is illustrated. As before, configuration 370 is applicable to a dialysis system employing any of the different types of pumping technologies described herein. FIG. 2A shows configuration 370 using different shelves or levels of a desk, night stand, etc. Configuration 370 is advantageous in one respect because supply bags may be tucked out of the way, leaving unit or machine 60 as the primary component that the patient views. As seen additionally in FIG. 2F, configuration 370 includes a bag stand 378, which orients supply bags 14, 16, and 22 in a position which allows gravity to help fluid travel from the supply bags to cassette 50. Stand 378 also organizes supply bags 14, 16 and 22 and includes or defines a plurality of notches or openings that hold the tubing or connectors, which extend from the supply bags. Bag stand 378 in one embodiment is made of vacuum-formed plastic or metal or is otherwise made of any suitable material.

Figure 2E:
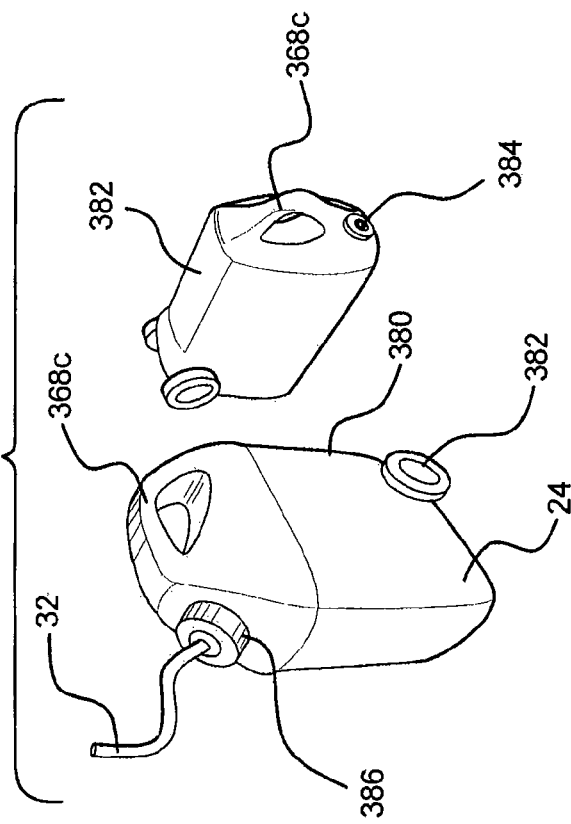
Figure 2D:
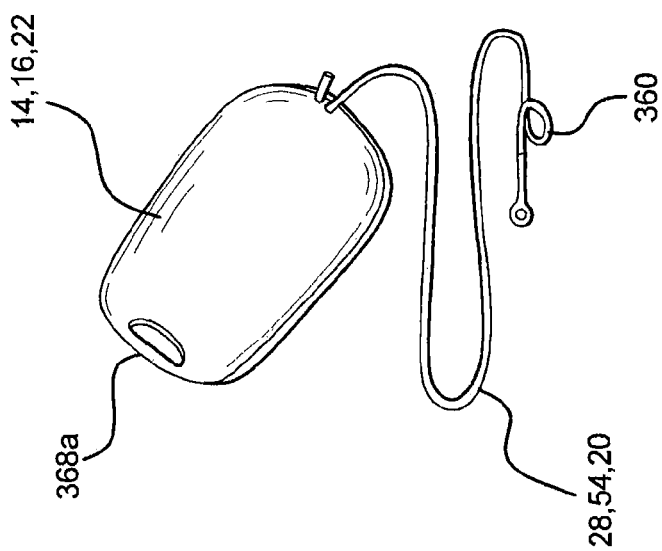

FIGS. 2A and 2E illustrate that configuration 370 includes or uses a reusable drain container 24, which in the illustrated embodiment includes a rigid or semi-rigid housing 380. Housing 380 defines or includes a handle 368c. In the illustrated embodiment, housing 380 is attached to wheels 382 which further aid in the transporting of the housing. FIG. 2E also shows that handle 368c is positioned so that housing 382 maybe tipped easily for drainage. To that end, an opening 384 of container 24 positioned so as to be located at the bottom of housing 380 when it is tipped over. Housing 380 of reusable drain container 24 includes a reusable cap 386, which when tightened on to mating threads of housing 380 compresses a ferral or other type of compressible apparatus or seal, located at the end of line 32, into a mating connector located or defined by housing 380.

FIG. 2B illustrates unit or machine 60 in more detail. As with unit 60 of configuration 350, unit 60 of configuration 370 is a single integrated machine in the illustrated embodiment. Cassette 50 is loaded into unit 60 horizontally as illustrated. Supply and drain tubes again enter device 60 from the front for easy access. Video monitor 66 is hinged so that it maybe adjusted to a suitable angle relative to a table or nightstand on which it is placed, while closing to form a compact and portable unit. Rotatable monitor 66 operates in conjunction with controls 62 and 64, which again can be off-screen input devices (e.g., membrane switches) or on-screen input devices that use a touch screen overlay. Unit 60 can also have a handle (not illustrated) or be provided with a bag or carrying case (not illustrated) for ready transport.

Referring now to FIG. 2C cassette 50 is shown loaded into unit 60. Cassette 50 includes an integrated fluid heating pathway 388. Integrated fluid heating pathway 388 can be a spiral path, which communicates with pathways located within the valve portion of cassette 50, such that to-and from-heater ports are not needed. Fluid heating pathway 388 operates with a heater 38 located within dialysis unit 60.

In the illustrated embodiment, patient line 12 and drain line 32 are preattached to ports of cassette 50. Drain line 32 can again have a larger diameter than patient line 12 for reasons discussed above. Cassette 50 also has fluid connector or ports 392, which connect to supply lines 20, 54, and 28. The supply lines or pigtails are preattached to supply bags, 14, 16 and 22, respectfully.

As seen additionally in FIG. 2C, patient line connector 362 located at the end of patient line 12 is pre-clipped or fastened to cassette 50 to orient the patient connector in proper position for priming. Further, drain line 32 and patient line 12 are coiled, so that cassette 50 can be moved more easily. Clamps 360 located at the ends of drain line 32 and supply lines 28, 54 and 20 can be color-coded as discussed above in connection with configuration 350. In an embodiment, connectors located at the ends of supply lines 28, 54 and 20 match with colors of luer connectors or ports 392 on cassette 50.

Figure 3C:
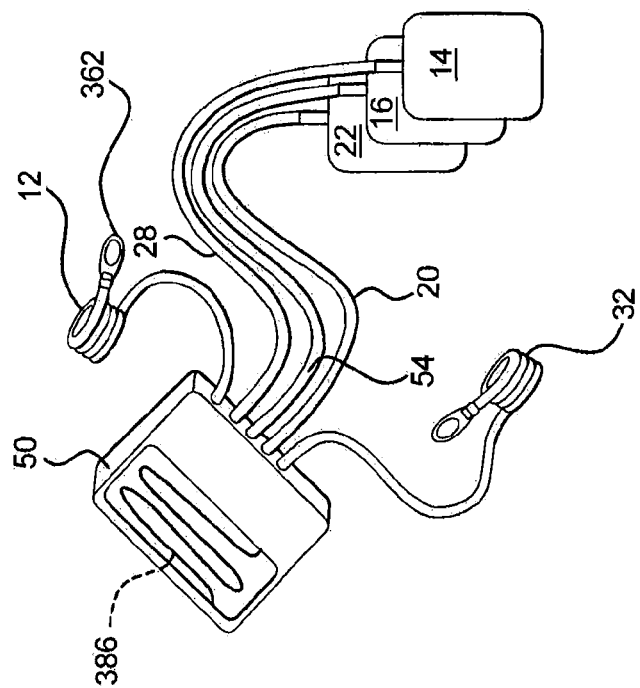
Figure 3B:
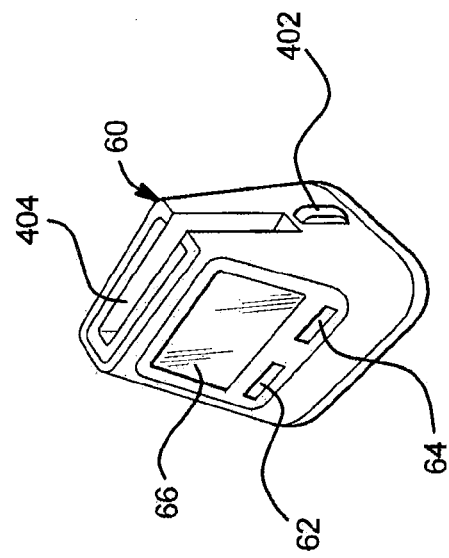
Figure 3A:
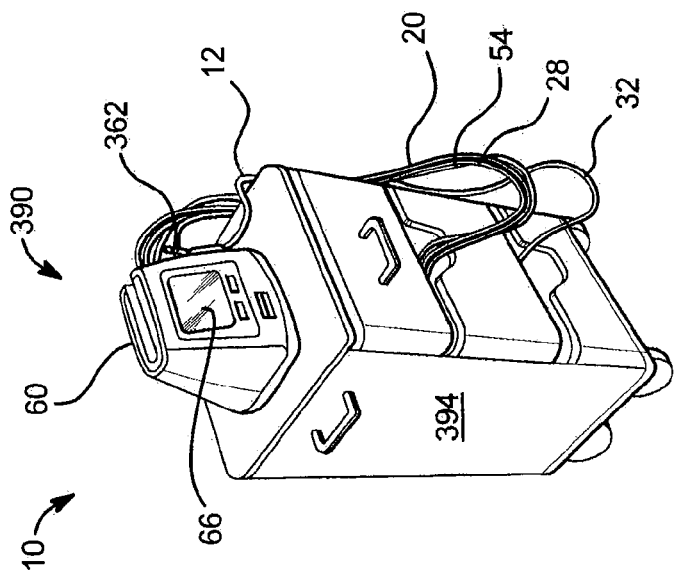

Referring now to FIGS. 3A to 3E, a third product configuration 390 is illustrated for system 10. Configuration 390 includes a dialysis machine or unit 60, having input devices 62 and 64 and a display device 66, including each of the alternative embodiments discussed above regarding those components. As seen in FIGS. 3A and 3E, configuration 390 is provided with an APD night stand 394. In FIG. 3E, a bottom drawer opening 396a receives a tray 398a. Tray 398a holds drain bag 24. In the illustrated embodiment, drain bag or container 24 is placed in a tray 398a, which is then slid into bottom opening 396a. A middle tray 398b holds supply bags 14, 16 and 22 and cassette 50 in a middle opening 396b. Tray 398b is shown in more detail in connection with FIG. 3D. Top drawer 398c located in top opening 396c can be used for extra supplies for example. Drain container 24 can be pre-attached to cassette 50 or reusable as discussed above.

As seen in FIGS. 3C and 3D, the disposal portion of configuration 390 in one embodiment is integrated, so that the patient does not have to connect any solution bag lines 20, 28 and 54. Also, patient line 12 and drain line 32 are pre-attached to cassette 50. Here, patient setup merely requires the patient to place patient line connector 362 located at the end of patient line 12 on a hook or other attachment device 402 provided on the housing of unit 60 for prime. The patient connects drain line 32 to drain bag or container 24 and places container 24 in lower tray 398a. As seen in FIG. 3D, solution bags 14, 16 and 22, which are preattached to cassette 50 are loaded together as packaged in tray 398b. Here, the patient pulls cassette 50 from tray 398b and places it into a vertical slot 404 defined by machine 60. Thus in configuration 390, cassette 50 is monitored vertically, which can be advantageous from an air separation stand point. Tubing connected to cassette 50 enters unit 60 via the side of cassette 50 in the illustrated embodiment. Cassette 50 includes an integrated fluid heating pathway 386, similar to or the same as that for configuration 370. Drain line 32 can also have a larger diameter than the supply and patient lines.

Display with Electromagnetic Compliance ("EMC") Seal

Referring now to FIG. 4, one embodiment of a display usable with any of the machines or units 60 (e.g., FIGS. 1B, 2B and 3B) described herein is illustrated by machine display 400. Display 400 includes a video display device 406. Video display device 406 is the component of machine display 400 that generates the various images, e.g., color or monochrome, seen by the patient. The metal case of video display device 406 makes intimate contact with an insulating dielectric film 408, which in turn makes intimate contact with an electrically conductive foam 410. One suitable display device 406 is provided for example, by Sharp Electronics, Color Thin Film Transistor ("TFT") Liquid Crystal Display ("LCD"), model LQ057. Suitable materials for insulative dielectric film 408 include polyester, polycarbonate and mylar. The material can have a thickness of about 0.003 inch (0.075 mm). One suitable material for electrically conductive foam 410 is made by Sehlegel or Insul-Fab, IFT-CF2-3030FR.

In an embodiment, conductive foam 410 is pressed against conductive coated ridge 412, which is built into or formed with the non-conductive machine casing 414. Ridge 412 extends around the perimeter of opening 416 defined by machine casing 414, positions window 418 within casing 414 and creates a surface for the conductive coating of ridge 412 to contact conductive foam 410. Electrically conductive foam 410 has a larger outer dimension than does transparent window 418, which in an embodiment is an optically transparent, impact resistant, plastic piece. Accordingly, the outer edges of conductive foam 410 extend beyond window 418 and thereby contact metal ridge 412. Insulating dielectric 408 is the same size or wider in the inner and outer dimensions than is conductive foam 410. Therefore, insulating dielectric 408 prevents conductive foam 410 from contacting the metal case of display device 406. Insulating dielectric 408 thereby provides an electrically isolating barrier between conductive foam 410 and metal display 406.

Conductive foam 410 contacts ridge 412 of machine casing 414 establishing an electrical connection. In this configuration, the conductive surfaces 410/412, the metal casing of display device 406 and the insulating dielectric material 408 sandwiched between those conductive surfaces form a capacitive electromagnetic compliance ("EMC") seal. A pressure sensitive adhesive ("PSA") 420 forms an environmental seal between transparent plastic window 418 and machine casing 414. That is, PSA 420 prevents dust and dirt from entering the inside of machine display 400 via opening 416. A mounting bracket (not shown) is fixed to machine casing 414, for example, via threaded couplers 422 welded to, heat staked or otherwise formed with machine casing 414. The bracket holds display device 406 and also compresses conductive foam 410 against display device 406 and ridge 412 of machine casing 414 to ensure good electrical contact between conductive foam 410 and the conductive coated ridge 412 of machine casing 414.

Machine display 400 takes advantage of the metal ridge 412 of casing 414, which surrounds window 418, and the metal casing of display device 406. The resulting EMC seal prevents electromagnetic energy ("EMI") generated by the electronics within machine casing 414 from exiting or passing through the casing 414 or display device 406. The EMC seal also prevents EMI generated by outside electronic devices from entering the machine through the paths just described. The above-described apparatus eliminates the need for shielding the entire display opening with an electrically conductive window, which adds expense and can also adversely effect image quality. Machine display 400 eliminates the need for an electrically conductive window altogether and thus eliminates the disadvantages just described.

Display with Elastomeric Keypad

Figure 5:
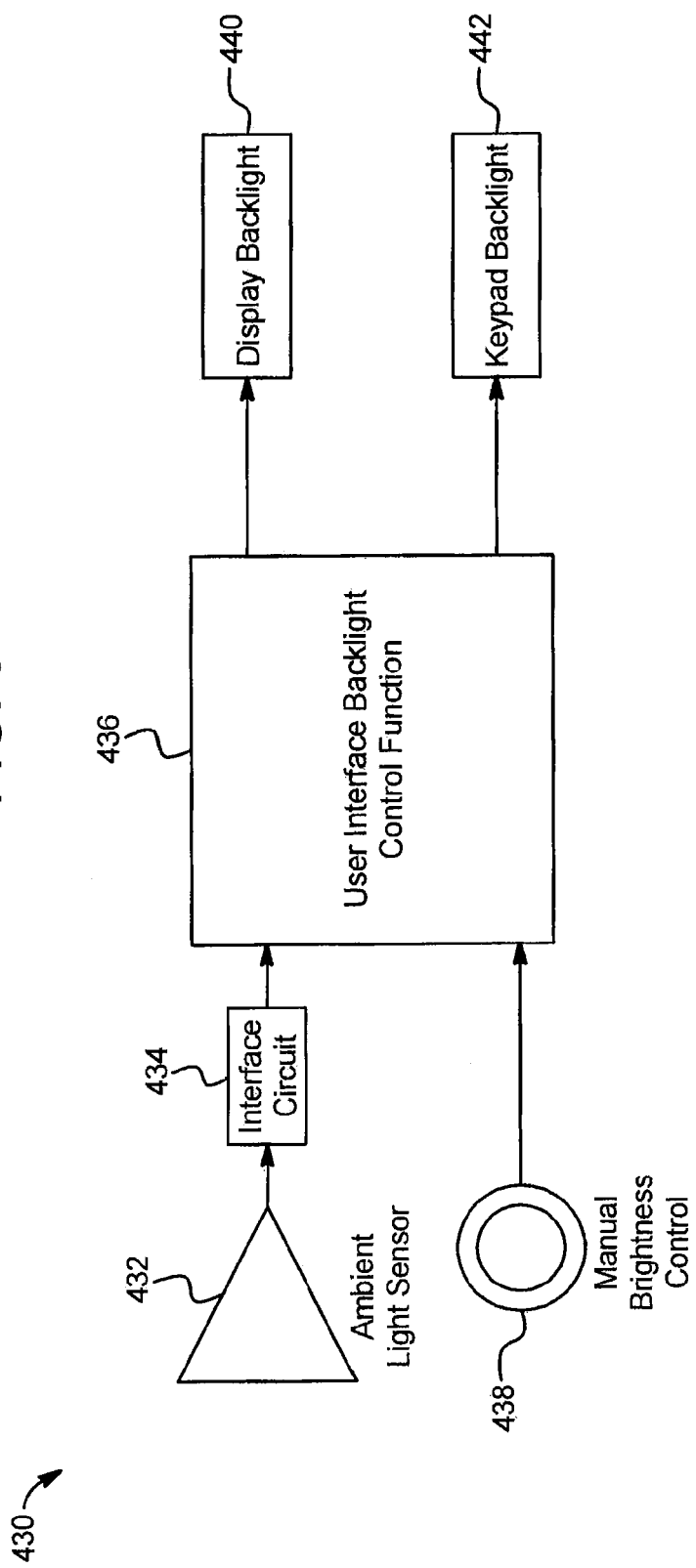
FIGS. 5 to 7 are schematic and elevation views showing one example of a user interface for a dialysis system employing the embodiments discussed herein.

Referring now to FIG. 5, one embodiment for a user interface operable with any of the machines 60 of system 10 (e.g., FIGS. 1A, 2A and 3A) is illustrated schematically by user interface 430. User interface 430 includes an ambient light sensor 432, and interface circuit 434, control electronics/control function 436, a manual brightness button or other type of manual input 438, a display backlight 440 and a keypad backlight 442. Any one or more of the above-listed components can be provided on a printed circuit board ("PCB") located within dialysis machine 60. In an alternative embodiment, interface circuit 434 is provided with sensor 432, located separately from the PCB.

Ambient light sensor 432 senses an amount of ambient light in the room in which machine 60 is positioned and sends a signal such as a zero to ten volt or 4 to 20 milliamp variable output signal to the interface circuitry 434. Interface circuit 434 conditions the signal from the ambient light sensor to make it readable or useful to the control electronics/control function 436.

Figure 6:
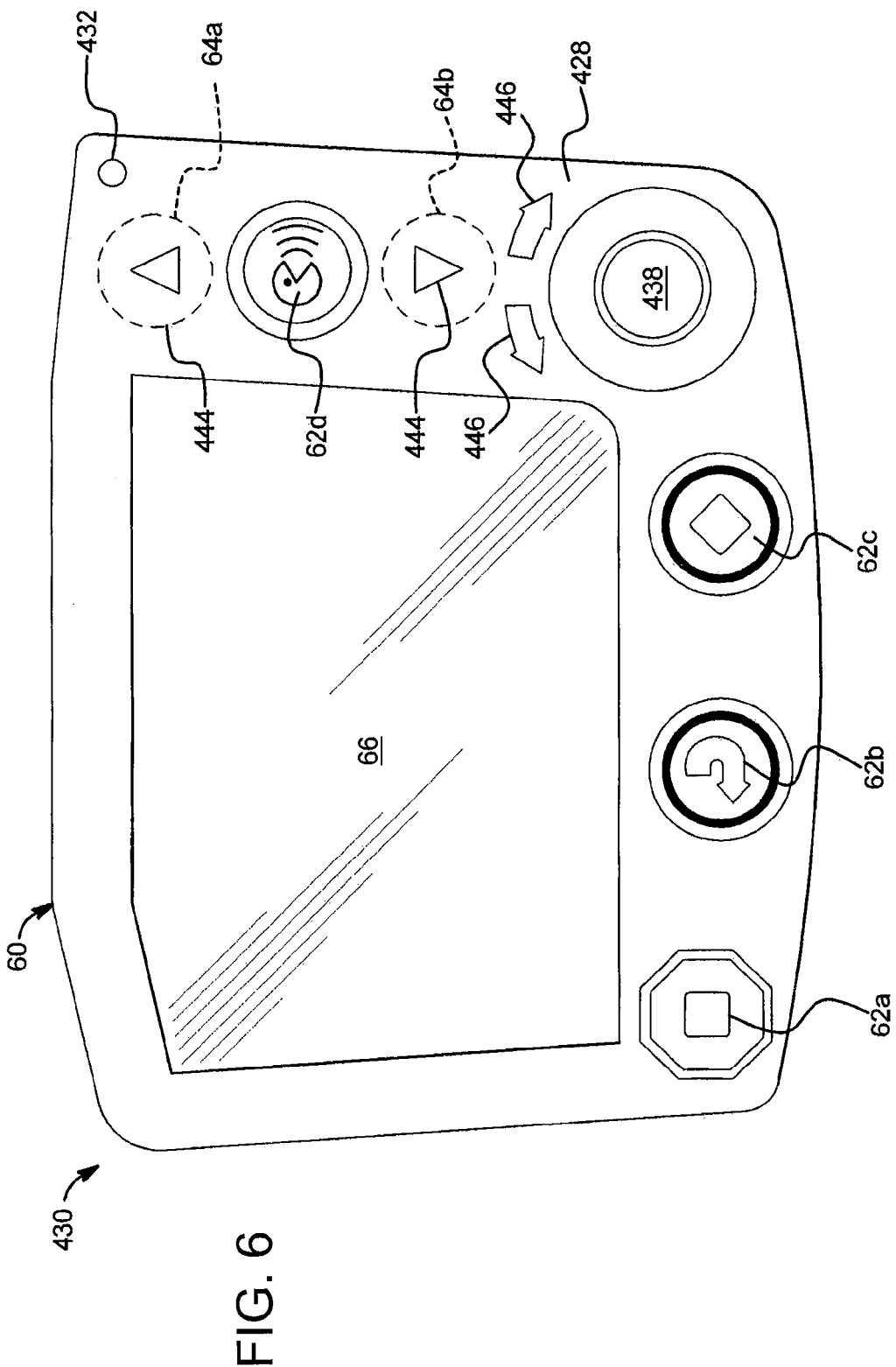

The user interface backlight electronics 436 also receives a variable input signal from manual brightness input or rotary knob 438. As described below in detail, input or knob 438 in one embodiment sets an initial brightness setting desired by the patient or operation. In an alternative embodiment, the signal from the manual brightness input 438 overrides the automatic backlighting provided via ambient sensor 432, interface circuit 434 and backlight electronics 436. As seen in FIG. 6, rotary knob operates with directional arrows 446.

Whether user interface backlight electronics 436 is controlled via sensor 432 and interface 434 or via a signal from manual controller 438, the user interface backlight control function 436 outputs a variable amount of power to display backlight 440 and keypad backlight 442. The power to display backlight 440 can be the same as the power to keypad backlight 442, or the power to one of the backlights can be different, e.g., scaled by a factor, of the power to the other backlight. For example, the keypad backlight may be controlled automatically to be slightly less bright than the display backlight 440 set initially via input 438 or vice versa. In an alternative embodiment, display backlight 440 can be controlled independently from keypad backlight 442. For example, although not illustrated, a second manual brightness control button, knob or controller can be provided, so that there is separate manual control of display backlight 440 and keypad backlight 442. The user or patient may want to set the display backlight to be more brightly lit, while the keypad backlight is set to be more dim or vice versa. Separate controls would also allow the user to turn one of the backlights off, while keeping the other on if desired.

It is expected that machine 60 (e.g., FIGS. 1B, 2B and 3B) will be operated in a varying ambient light environment because the machine may be used to perform dialysis at home and at any time during the day or night. For example, the machine may be set up at night under normal room light conditions and perform therapy thereafter while a person sleeps with the lights off. Machine 60 at any time during therapy may need to warn the patient of an error or alarm and wake the patient potentially in a dark or dimly lit room. User interface 430 including automatically variable lighting automatically adjusts backlight intensity to compensate for changes in ambient light level so that such errors or alarms may be seen easily.

FIG. 6 shows machine 60 operating with variable ambient light user interface 430. Ambient light sensor 432 is positioned to receive light impinging on machine 60. Light sensor 432 in an embodiment includes a photo receptor having a spectral response approximately that of the human eye, such as an LX1970 Visible Light Sensor provided by Microsemi Corporation, Garden Grove, Calif. This sensor includes processing that provides a photopic light wavelength response curve that nearly duplicates that of the human eye. Control function 436 shown in FIG. 5 sets the display and keypad backlight brightness 440 and 442, respectively, to the level set by the user and modifies the backlight in response to changing ambient light levels. For example, control function 436 can be configured so that an increase in ambient results in a corresponding increase in display and keypad backlight intensity 440 and 442. Conversely, a decrease in ambient light results in a corresponding decrease in display and keypad backlight intensity 440 and 442. Backlight control function 436 also compensates for any non-linearity of ambient light sensing. Backlight control function/electronics 436 can be a dedicated analog circuit, a dedicated digital circuit (such as a microcontroller), hybrid of both or be a functional element of a shared-embedded application processor. The function may also be implemented on an application specific integrated circuit ("ASIC").

As discussed above, the patient adjusts the ambient light setting via adjustment device 438, which includes a dial or knob for example. Device 438 controls a variable electrical output signal to backlight control function 436. Function 436 can be set to time-out after a period of non-adjustment, following a period of adjustment or control 436 to know when the desired setting has been made. Thus after the patient changes the desired amount of light, circuitry 434 waits a period of time after the change to know that the change has been set. After this amount of time, control function/electronics 436 is set to assume that the desired backlight setting has been made.

The setting can be made in any ambient condition. Control function/electronics 436 is configured to modify its output if the ambient conditions change, so that the overall backlight brightness level stays at the level set by the user. For example, if the patient sets a desired level during normal lighting conditions to a high backlit level and then night falls or the patient turns out room lights, electronics 436 would decrease the power to display and keypad backlights 440 and 442 and maintain the relative brightness between the display and keypad backlights 440 and 442 and the ambient light. In this embodiment, a fixed level is adjustable after which circuitry 434 adjusts the backlight display and keypad backlights 440 and 442 to achieve or maintain that setting made by the patient. In another embodiment, manual control or rotary knob 438 overrides an automatic, e.g., optimized setting made in software in which power is adjusted based on ambient light compared to the automatic setting.

In an alternative embodiment, control function 436 is configured to compensate for the human eye's change in sensitivity due to ambient light levels integrated over time. As is known, the longer a person resides in the dark, the more sensitive the person's eye becomes. This phenomenon is sometimes termed as "dark adaptation" or "unaided night vision." In this alternative embodiment, control function 436 would gradually reduce power to one or both of display backlight 440 and keypad backlight 442 over time and over a steady ambient light reading via sensor 432. This feature in an embodiment is performed only when control function 436 determines that it is dark enough to do so, such as at a particular ambient light, read from sensor 442, or lower.

Figure 7:
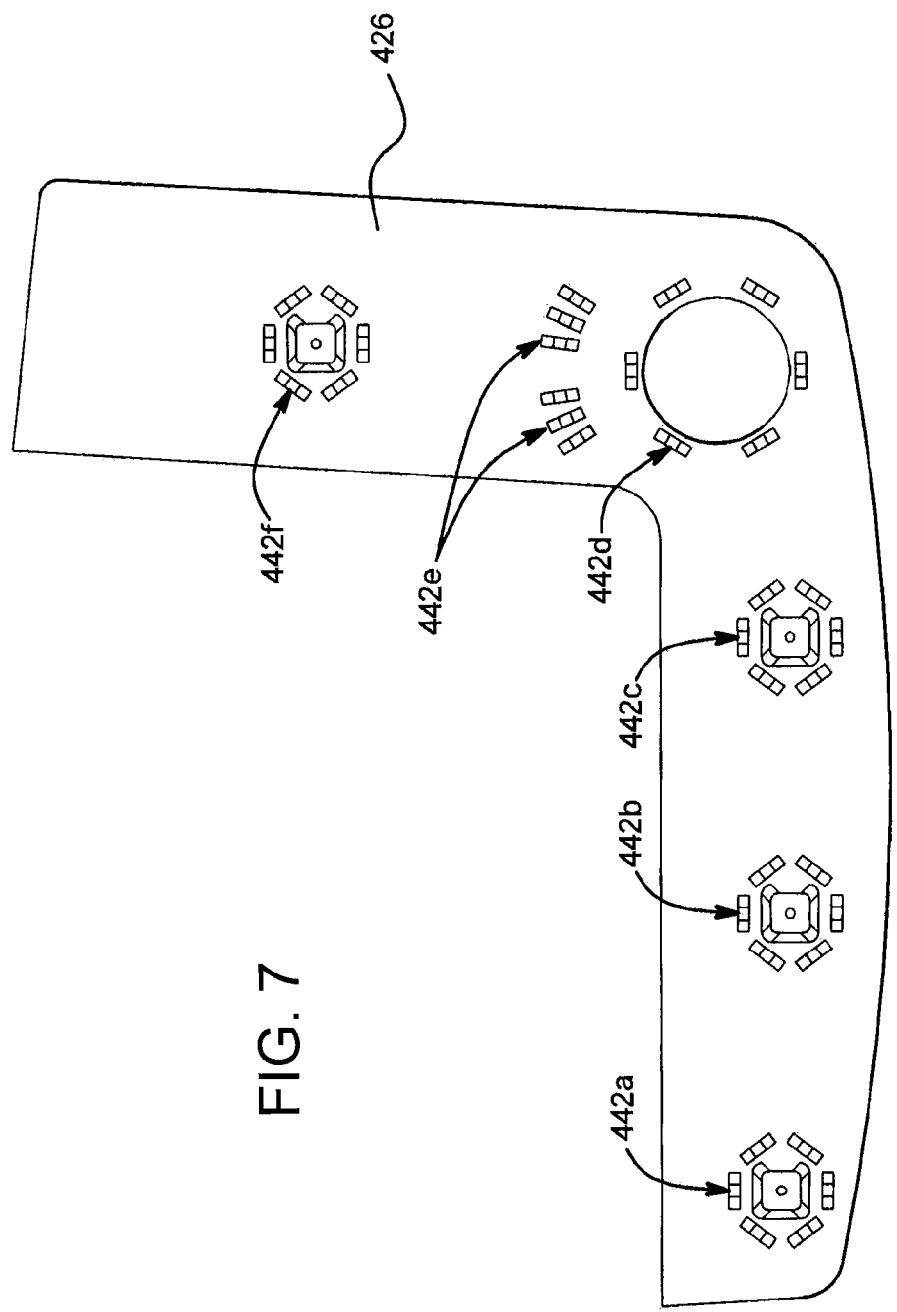

In FIG. 6, user interface 430 includes buttons that are visible to the user, such as buttons 62a to 62d. User interface 430 also includes "hidden" buttons or inputs 64a and 64b. In an embodiment, visible buttons 62a to 62d are three dimensional and raised to allow the patient to have enhanced finger traction and feel and for ease in locating a desired function. Buttons 62a to 62d provide tactile feedback when pressed. Each visible button 62a to 62d includes a three dimensional icon or indicia, which can be raised or inset so that a visually impaired person can identify a particular button through touch alone. Visible buttons 62a to 62d in an embodiment are color-coded or otherwise unique visually and/or tactilely to further aid in their identification. As seen in FIG. 7, each visible button 62a to 62d is backlit individually, wherein control function 436 of FIG. 5 can be configured to light only buttons which are currently operational.

Hidden buttons 64a and 64b are provided behind front panel 428. Inputs 64a and 64b are accordingly shown in phantom. Front panel 428, however, may include indicia 444 that mark the areas of hidden buttons 64a and 64b. The patient presses icons 444 displayed on front panel 428 to activate hidden buttons 64a and 64b. Hidden buttons 64a and 64b can also provide tactile feedback through front panel 428 to inform the patient that the hidden button is being activated. Further, the patient can view changes occurring on video monitor 66 to receive such feedback and recognition. Hidden buttons 64a and 64b are advantageous for certain applications, including but not limited to nurse mode or service mode buttons or other buttons that are not used typically by the patient but used instead by clinicians or service personnel.

Although four visible buttons 62 and two hidden buttons 64 are illustrated, user interface 430 can have any suitable number of visible and hidden buttons, which can be push type buttons, rotary knobs, such as rotary knob 438, toggle switches, maintained or momentary buttons, sliding input devices, and any suitable combination thereof.

As discussed throughout this application, electromechanical buttons 62 (referring collectively to button 62a to 62d) and hidden buttons 64 (referring collectively to buttons 64a and 64b) can instead be provided on a touch screen overlay, which operates with video screen 66. It is advantageous to use the electromechanical configuration in one respect because the electromechanical buttons allow for the buttons to be three-dimensional, which enhances tactile feedback and recognition.

Referring now to FIG. 7, a light emitting diode ("LED") board 426 is illustrated. LED board 426 shows different patterns for keypad backlighting 442 (442a to 442f) discussed above in connection with FIG. 5. In particular, LED board 426 includes backlight pattern 442a operable with visible button 62a (FIG. 6), backlight pattern 442b operable with visible button 62b (FIG. 6), backlight pattern 442c operable with visible button 62c (FIG. 6), backlight pattern 442d operable with rotary knob 438 (FIG. 6), backlight pattern 442e operable with directional arrows 446 (FIG. 6), and keyboard backlight pattern 442f operable with visible button 62d (FIG. 6). Patterns 442a to 442f are arranged as desired to provide a desired amount and spacing of backlighting behind buttons 62 (62a to 62d) and control knob 438. As discussed previously, LED arrangements 442a to 442f can be lit individually, so that only active buttons are lit for example. This can help in machine setup and operation to guide the patient through different screens of therapy.

Low Battery Disconnect Circuit

Figure 8:
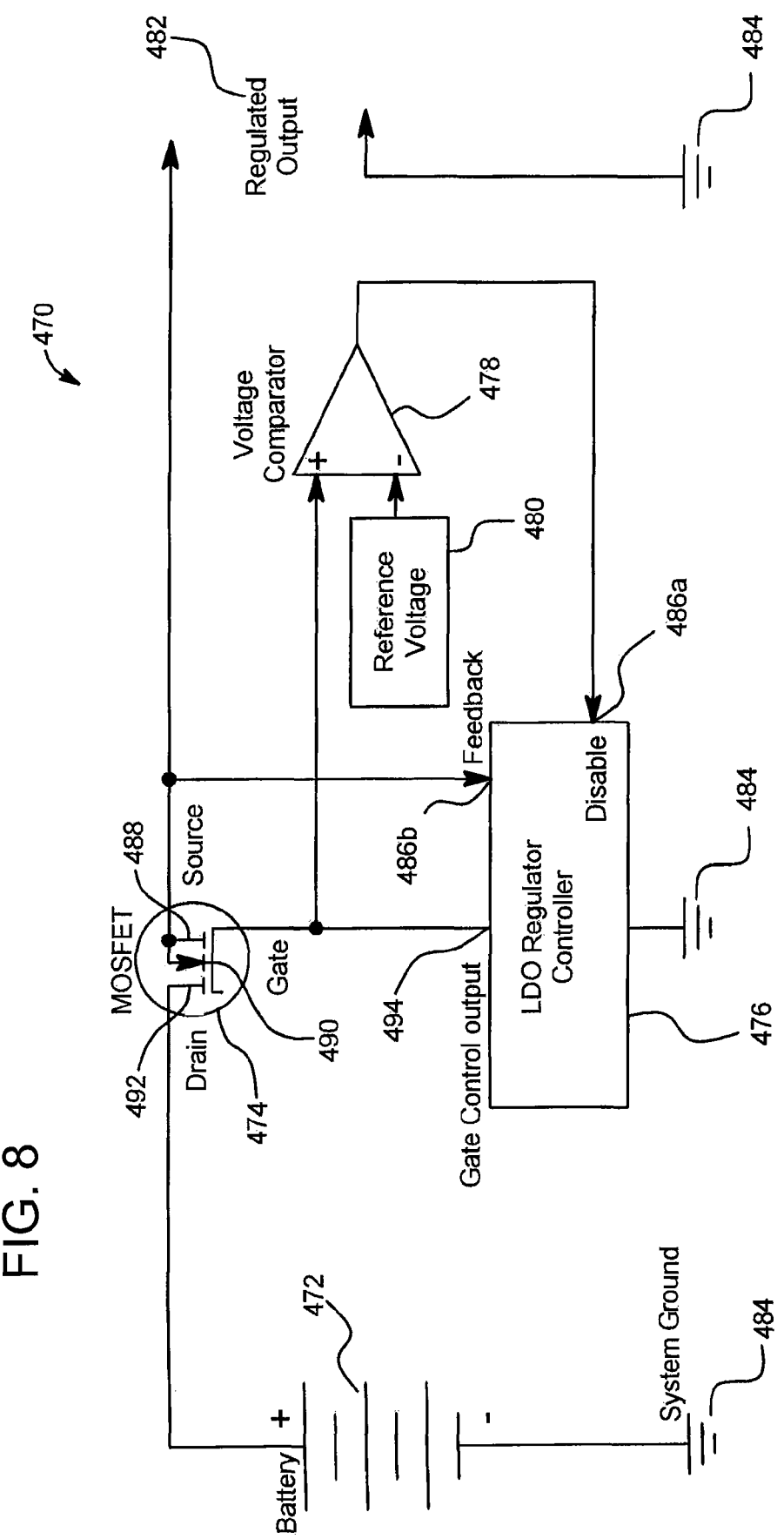
FIGS. 8 and 9 are schematic views illustrating one example of a system employing the embodiments discussed herein having a low battery disconnect circuit.
Figure 9:
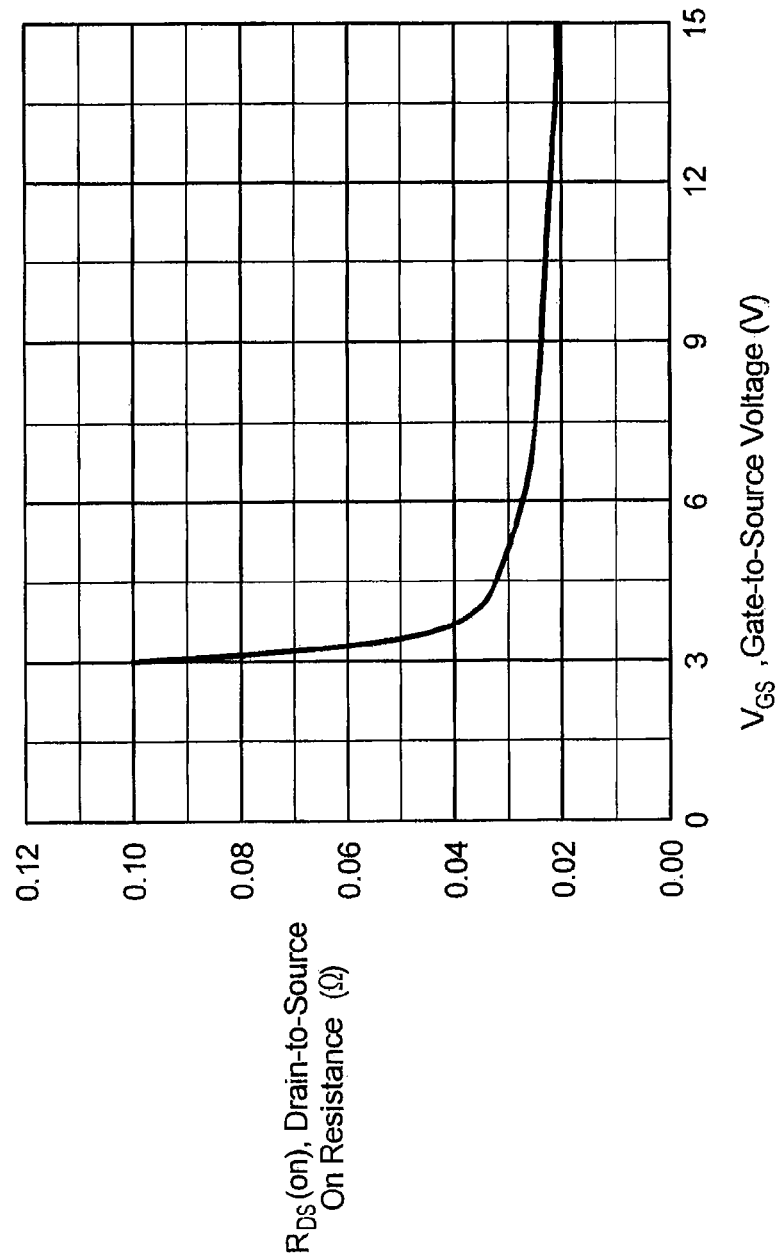

Referring now to FIGS. 8 and 9, circuit 470 illustrates one embodiment of a low battery disconnect circuit used with the electronics and user interface of system 10. Circuit 470 is located within control unit 60 (e.g., FIGS. 1B, 2B and 3B) and in an embodiment is provided on a printed circuit board, such as a delegate circuit board, which communicates with a supervisory PCB. Circuit 470 provides back-up power to machine 60 in an event that the main power source is interrupted. When the back-up power is used its output voltage level gradually declines over time as is known. The electronics driven by the battery back-up however need a steady voltage to operate reliably. A voltage regulator can be used to regulate the voltage at a steady level. As battery voltage declines, the regulator reaches a point that it cannot hold the voltage output steady based on the voltage it sees from the battery. If the duration of the main power source interruption continues long enough, the battery discharge continues to the point that loss of regulation occurs. When this happens the machine must be shut-down. This result should be avoided to ensure reliable machine operation. Circuit 470 enables the disconnect point to be safely near the point of loss of voltage regulation. Accordingly, circuit 470 lengthens the amount of time that machine 60 can run on battery back-up.

Circuit 470 includes a battery 472, a metal oxide semiconductor field effect transistor ("MOSFET") 474, a voltage regulator 476, a voltage comparator 478, which receives a reference voltage 480, a regulated voltage output 482 and system ground 484. A negative terminal of battery 472, the voltage regulator 476 and the regulated voltage output 482 are all referenced to system ground 484.

Voltage regulator 476 receives a disable input 486a from voltage comparator 478 and a feedback input 486b from the source 488 of MOSFET 474. Regulator 476 also provides a voltage output 494 to the gate 490 of MOSFET 474 as well as to a positive terminal of voltage comparator 478. One suitable voltage regulator 476 is provided by Micrel Semiconductor Inc, San Jose, Calif., part # MIC 5158, which is used in combination with a latch (not illustrated) that latches the disabled state. The positive terminal of battery 472 is connected electrically to the drain 492 of MOSFET 474.

Circuit 470 takes advantage of an inherent characteristic MOSFET 474, which is an on-resistance versus gate voltage characteristic. FIG. 9 illustrates this characteristic. The characteristic is as follows. As discussed, the voltage of battery 472 needs to be higher than the regulated output 494 of voltage regulator 476 to provide a linear regulator typology. For example, the starting voltage of battery 472 can be six VDC, while the regulated output 494 is five VDC. The initial fully charged battery 472 can actually have a voltage of 6.1 VDC, for example. A voltage reference 480 supplied to the negative terminal of voltage comparator 478 in this example could be five VDC. Regulator 494 compares feedback voltage 486b to the voltage reference and adjusts its output 494 to gate 490 of MOSFET 474 so that the regulated output 482 is five VDC.

When drain 492 of MOSFET 474 for example sees an initial voltage 6.1 VDC from battery 472 and source 488 is set to five VDC, a voltage drop ("VDS") of 1.5 VDC occurs across MOSFET 474. As voltage of battery 472 declines, regulator 476 increases its output 494 at gate 490 of MOSFET 474, which decreases the drain to source on-resistance as seen in FIG. 10, and which therefore reduces the voltage drop across MOSFET 474 to maintain the voltage at MOSFET source 488 to be 5 VDC.

In circuit 470, MOSFET 474 therefore acts like a variable resistor. If for example the load being driven by regulated output 482 is drawing 1 Amp and batter 472 has already been drained to the point at which its voltage is 5.1 VDC, the drain-to-source voltage ("VGS") is 0.1 VDC and the drain-to-source resistance is 0.1 Ohms (0.1 VDC÷1 Amp=0.1 Ohm). When RDS is at 0.1 Ohm as seen in FIG. 10, VGS is about three VDC. As battery voltage continues to decline, the operating point of MOSFET 474 moves down along the curve of FIG. 9. Here, regulator 476 continues to increase VGS, while the resistance of MOSFET 474 continues to decrease in compensation.

As seen in FIG. 9, when RDS drops to about 0.03 Ohm, the curve begins to flatten considerably, so that VGS has to increase more and more dramatically to effect the same change in RDS. When VGS reaches 12 VDC, the curve is almost completely horizontal, meaning MOSFET 474 is almost fully on and RDS is about 0.022 Ohm. Here the threshold of comparator 478 is finally reached or surpassed when VGS becomes more positive than the threshold voltage. When VGS reaches this 12 VDC threshold in the example, comparator 478 switches and regulator 494 becomes disabled, driving VGS to zero, disconnecting battery 472 from the load connected to regulated output 482 effectively.

In one embodiment, the minimum achievable RDS for MOSFET 474 is about 0.02 Ohm. Regulator 476 is chosen such that it can drive VGS to at least 15 VDC, so that RDS can reach 0.02 Ohm according to FIG. 10. If it is assumed again that the load driven by regulated output voltage 482 is one Amp, then for example VDS is 0.02 VDC at the minimum RDS of MOSFET 474 of 0.02 Ohm. In the example, the lowest voltage that battery 472 could provide to yield a regulated output voltage at 482 would therefore be 5.02 VDC. Reference voltage 480 for comparator 478 is set in one embodiment to 12 VDC. As discussed above, this yields an on-resistance of 0.022 Ohms, which in the one Amp example occurs when battery voltage drops to 5.022 VDC. Thus, the theoretical minimum for battery 472 is 5.02 VDC, while the actual sustainable voltage minimum for battery 472 is 5.022 VDC. This results in a mere loss of 2 millivolts above the theoretical limit.

Circuit 470 accordingly provides topology that allows for lower tolerances and therefore lower precision and thus lower cost parts to be used in a safe and reliable circuit. It should be appreciated that even if the actual to theoretical low voltage output varies by plus or minus 25%, the resulting disconnect threshold varies by less than 5 millivolts. It should also be appreciated therefore that circuit 470 eliminates the need for a precision comparator function and safety margin, which has been used in the past to ensure that the threshold does not drop below the level at which regulation can be maintained. Adding a safety margin means that the nominal threshold voltage is moved higher, which results in a disconnected or battery voltage higher than that achievable with a topology of circuit 470. Disconnecting at a higher voltage means less time available to operate on battery back-up.

In an alternative embodiment, the output of comparator 478 is used to trigger an interrupt to one or more processors of system 10, trigger a delay circuit (not illustrated) and have the output of the delay circuit trigger the shutdown of system 10. This approach signals to the one or more processor that power is to be disconnected shortly, giving the processor an opportunity to prepare for shutdown of system 10. For example, the system could send an alarm to the patient, close one or more valve, ramp down one or more pump and record the status of therapy (such as the amount of fluid pumped per current cycle, amount of ultrafiltrate removed, etc.) and perform any other safety measure needed to prepare for shutdown.

It is also contemplated to use circuit 470 or the alternative interrupt circuit to notify a processor whenever a switch to battery back-up occurs, wherein the processor has the further capability to shut off power. In such case, circuit 470 or the alternative interrupt circuit can provide a back-up shut-off circuit in case the processor fails to shut itself off.

In a further alternative embodiment, a second comparator is provided having a voltage threshold less than that of comparator 478. The lower threshold voltage second comparator generates a processor interrupt signal when VGS becomes more positive than the threshold voltage. The higher threshold voltage of comparator 478 causes the system to be shut down when VGS becomes more positive than the higher threshold voltage. This causes a time delay.

Silent Alarm Capability/Remote Alerting

Referring now to FIG. 10, one embodiment of system 10 having a silent alarm capability is illustrated. As discussed above, it is desirable in certain circumstances not to have machine or unit 60 of system 10 (e.g., FIGS. 1A, 2A and 3A) sound an alarm itself. For example, unit 60 may have to be located near other sleeping people who do not need to be awoken upon an alarm condition. In other instances, the patient and/or patient's spouse can be hearing impaired or deaf and not be able to respond to an audible alarm from unit 60 of system 10. As discussed below, the silent alarm capability of system 10 solves these dilemmas.

FIG. 10 shows the machine 60, which is configured similar to that shown in connection with FIG. 3B. It should be appreciated, however, that the silent alarm capability can be provided with any of the machines 60 described herein for system 10. Machine 60 houses a transmitter 500. One suitable transmitter 500 is provided by Harris Corporation SC-DOT1003-1 transmitter. Another suitable transmitter is an Alert Master Model 6000, part number AMER-AM 6000.

In an embodiment, transmitter 500 is microprocessor controlled. The microprocessor in an embodiment is provided on a safety controller or safety PCB, which operates with a supervisory microprocessor. The integration of transmitter 500 and microprocessor control helps to prevent false alarms because the microprocessor decides when transmitter 500 should send signal 502.

Transmitter 500 transmits a radio frequency ("RF"), microwave, ultrasonic or infrared signal 502, which can be received by one or more remote receiver. For example, the remote receiver can be a remote alarm, headset or computer 504, which generates a visual or audible alarm in a place located remotely from machine 60. Alarm 504 alerts a caregiver or relative that machine 60 of system 10 is experiencing an alarm condition. Video monitor 66 of machine 60 posts an alarm message 506, which can (i) describe the nature of the alarm and/or (ii) provide a suggested course of corrected action. Signal 502 can be continuous, e.g., for three seconds, or pulsed as desired.

In an alternative embodiment, transmitter 500, as provided by Harris Corporation CC-PS1001, Private Page, is a local wireless paging system that sends its signal 502 to a remote pager or cellphone 508. Pager or cellphone 508 is worn by a caregiver or relative. The pager responds to signal 502 in a known manner, alerting the caregiver or relative to proceed to machine 60 and observe visual message 506.

In still a further alternative embodiment, transmitter 500 sends signal 502 to a bed shaker 510. One suitable bed shaker is provided by Harris Communications Super-Shaker Model SA-SS120V, 120VAC. DC Model is SA-SS12V. Bed shaker 510 is placed beneath the patient or is otherwise coupled to the patient's bed, so that the patient is awakened upon an alarm. This can be done so as not to wake other people nearby.

In further alternative embodiments, signal 502 can be sent to any combination of remote alarm 504, pager 508 and/or bed shaker 510. Further, machine 60 can be configured with one or more speakers 512. Speakers 512 provide an audible alarm at machine 60, which can be made in lieu of or in addition to the signaling of the remote devices. Speakers 512 can alternatively provide an audible version of message 506, which audibly tells the patient, caregiver or relative what to do to correct the current alarm condition. For example, signal 502 can be sent to remote alarm 504 or pager 508, alerting a person to come to machine 60, at which point the person hears an audible message from speaker 512 informing the person of the nature of the alarm and likely corrective action.

In any of the previously mentioned embodiments involving transmitter 500, the transmitter 500 exist alternatively externally to machine 60 and its display 66. This is done via an external interface connection through machine 60. The interface of machine 60 provides a polar/binary signal, ON/OFF signal or data stream interface, such as serial or parallel interface, depending upon the type of remote transmitter 500 used.

Graphical Display of Progress Dialysis Treatment Steps

Referring now to FIGS. 11A to 11G, screen shots of video monitor 66 of dialysis machine 60 of system 10 (e.g., FIGS. 1A, 2A and 3A) illustrate a fill cycle, such as a PD fill cycle graphically via a character 520. As shown here and in subsequent figures, character 520 is used throughout the therapy, to provide the patient with a consistent and familiar treatment display.

In the illustrated embodiment, a character 520 is shown as an animated drinking glass. It should be appreciated, however, that character 520 can have other suitable forms, shapes and/or indicia. In one embodiment, different characters or shape of a same character are provided as choices to the patient in a set-up mode. The character or shape chosen is used thereafter throughout the screens to display therapy progress and other information discussed below. The patient can change the character or shape at any time or in between treatments.

In a preferred embodiment, character 520 has a friendly appearance, which also aids in relieving the stress of treatment. Character 520 adds a human element to therapy and provides useful information to the patient. It is contemplated that when such information is presented in a user-friendly format, the patient has a better probability of receiving and understanding the information.

In the fill cycle of FIGS. 11A to 11D, glass 520 is shown initially empty in FIG. 11A and is filled incrementally in FIGS. 11B and 11C, before being filled completely in FIG. 11D, indicating that the fill cycle is complete. Character 520 includes or has a therapy indicator 522, which in the illustrated embodiment is a hand extending from the body of glass 520, which points to or otherwise indicates which cycle of the therapy is currently underway. An up arrow 524a is provided initially to illustrate that the level of dialysis fluid is increasing, i.e., that a fill cycle is occurring. The water level in glass 520 on the other hand indicates a stage of a particular cycle. A fuller glass indicates that a later portion of the current cycle is taking place. The indicia of character 520, e.g., the face shown on the glass, is also consistent with the fact that system 10 is currently in an active, e.g., fill mode.

Figure 12:
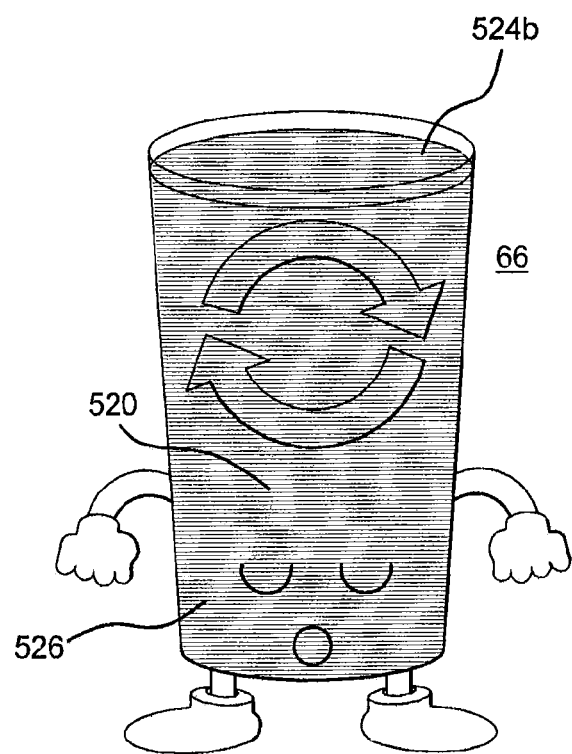
FIG. 12 is a machine screenshot illustrating an embodiment of a graphical depiction of a dwell cycle of a dialysis system employing the embodiments discussed herein.

Referring now to FIG. 12, a screen shot of video monitor 66 illustrates a dwell cycle, which occurs after the patient's peritoneum has been filled with a fill volume of dialysate. The dwell cycle is a relatively inactive cycle for system 10. Machine 60 is not pumping liquid to or from the patient. Thus, indicia 526 illustrates that the glass appears to be resting or sleeping. Up arrows 524a (FIGS. 11A to 11D) are replaced by circular or dwell arrow 524b. Dwell arrow 524b indicates that the volume of fluid within the patient's peritoneum is currently not changing but is instead circulating or moving within the patient to remove waste and toxins. Glass 520 remains full of fluid during this period because the patient's peritoneum also remains full of fluid.

Referring now to FIGS. 13A to 13D, character 520 animates a drain cycle. Animations for any of the cycles can be cartoon animations, video clips and any combination thereof. Here, glass 520 is drained progressively in FIGS. 13A to 13D to indicate that drain is taking place and how much of the drain cycle has occurred. Glass 520 is full at the beginning of the drain cycle in FIG. 13A. At the end of the drain cycle in FIG. 13D, glass 520 is emptied completely, indicating the end of the drain cycle. Character indicator 522 and down arrow 524c both point downward, indicating fluid is leaving the patient, that is, indicating that machine 60 is currently in a drain cycle.

Any of the fill, dwell and drain cycle sequences can be accompanied by an elapsed time display, a time remaining display, an indication of whether the cycle, e.g., drain cycle is a first drain cycle, a second drain cycle, for example. The face of glass 520 also indicates that the glass is awake, e.g., that machine 60 of system 10 is in an active pumping cycle.

In an embodiment, the filling of glass 520 in any cycle occurs continuously, that is, the fill level is moving continuously albeit slowly during a particular cycle. In another embodiment, the level changes after an increment of time, e.g., every ten seconds, every thirty seconds, every minute, every five minutes, etc. Or, the level changes after an increment of volume, e.g., after every 10 millimeters pumped, 30 millimeters pumped, etc. The filling of glass 520 is also tied to other events that occur during treatment that may stop the filling. For example, if an alarm condition occurs in which pumping is stopped, video monitor 66 is configured to stop the display of the filling of glass 520.

Figure 16:
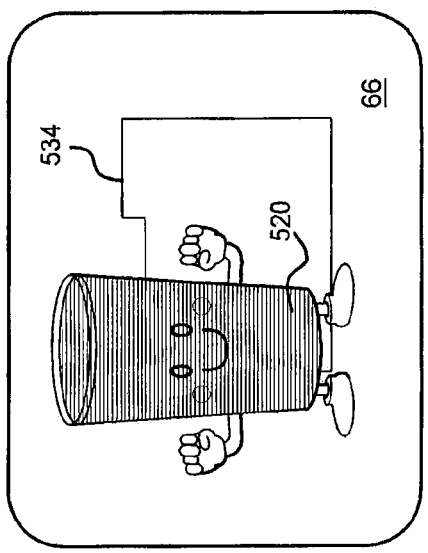
FIG. 16 is a machine screenshot illustrating an embodiment of a graphical depiction offering patient information for a dialysis system employing the embodiments discussed herein.
Figure 15:
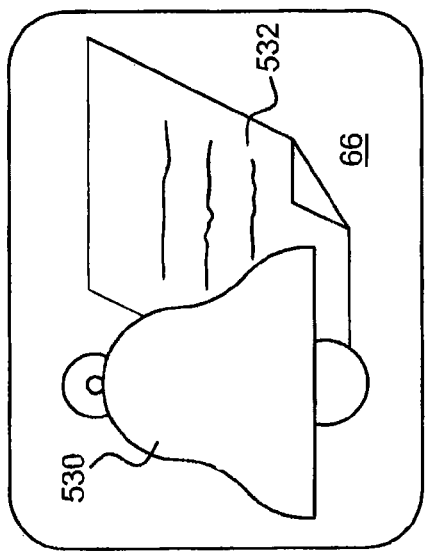
FIG. 15 is a machine screenshot illustrating an embodiment of a graphical depiction offering alarm information for a dialysis system employing the embodiments discussed herein.
Figure 14:
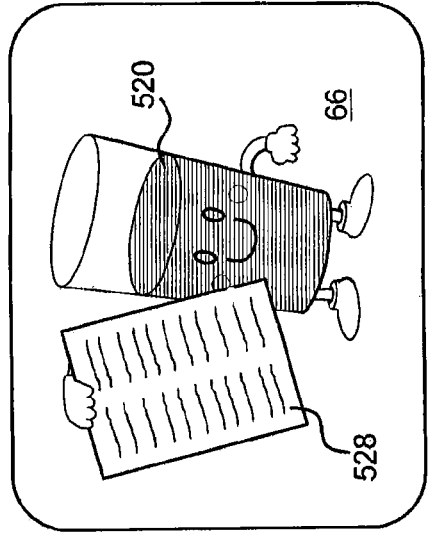
FIG. 14 is a machine screenshot illustrating an embodiment of a graphical depiction offering treatment information for a dialysis system employing the embodiments discussed herein.

Referring now to FIGS. 14 to 16, video monitor 66 is further configured to display other aspects of therapy, such as PD. As seen in FIGS. 14 and 16, character 520 is used in certain of these additional displays, while FIG. 15 illustrates that character 520 does not have to be displayed in each screen shot or for each feature of system 10.

FIG. 14 illustrates a therapy report or therapy tracking screen in which character 520 holds a report 528 indicating that particular parameters of a previous treatment or therapy have been recorded. In an embodiment, video monitor 66 operates with a touch screen overlay, in which case the patient can press therapy report 528 to review treatment information. Treatment information can include any potentially desirable information, such as, treatment time, volume delivered, fill times, dwell times, drain times, number of cycles, UF removed, average dialysate temperature, alarm information, etc. In an alternative embodiment, electromechanical inputs, such as visible buttons 62 or hidden button 64 are used to recall information indicated by therapy report 528.

FIG. 15 illustrates an alarm screen, which includes an alarm indicator 530 and an alarm report 532. In an embodiment, the screen of FIG. 15 is displayed upon an alarm condition. If video monitor 66 operates with a touch screen overlay, either one or both of alarm indicator 530 and alarm report 532 can be touched to cause visual, audio or audiovisual alarm information to be given to the patient. In an alternative embodiment, the screen of FIG. 15 is shown at the end of treatment so that the patient can review a separate alarm report 532 to learn of any alarm conditions that occurred during the previous therapy or to learn of any alarms that have occurred over recent therapies, such as over the last week or month.

In FIG. 16, video monitor 66 shows a patient information screen. Here, character 520 is shown in combination with a file or folder 534, which represents a patient file or patient history. Here again, if video monitor operates with a touch screen overlay, file 534 can itself be selected to show patient history, treatment parameters, background information and any other desirable patient-specific information. Otherwise, electromechanical inputs are used.

In an embodiment, the screens of FIGS. 14 to 16 are sub-screens obtained selectively via a main screen or supervisory sub-screen. Sub-screen selection can be done via a touch screen input or via electromechanical input, such as a scrolling input device that enables the patient to scroll through the icons representing the different screens (e.g., characters 520 in different settings) before selecting one of the icons to display the selected screen.

Figure 19:
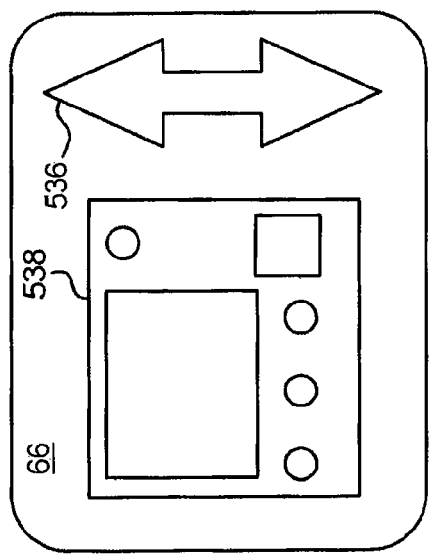
FIG. 19 is a machine screenshot illustrating an embodiment of a graphical depiction allowing the patient to change alarm settings in a dialysis system employing the embodiments discussed herein.
Figure 18:
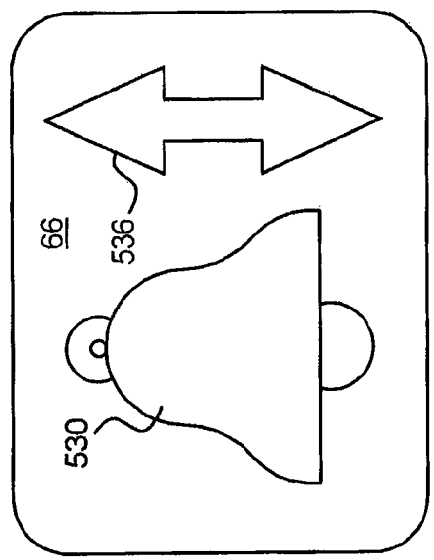
FIG. 18 is a machine screenshot illustrating an embodiment of a graphical depiction allowing the patient to change alarm settings in a dialysis system employing the embodiments discussed herein.
Figure 17:
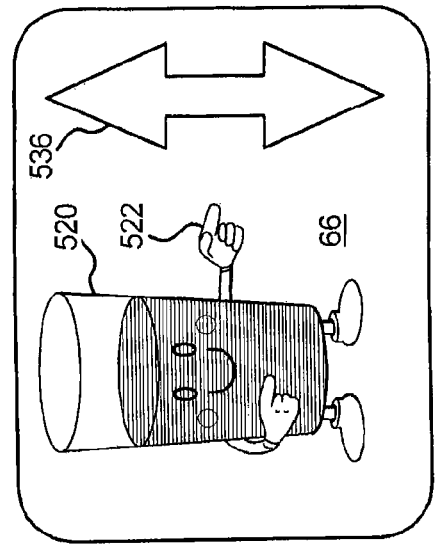
FIG. 17 is a machine screenshot illustrating an embodiment of a graphical depiction allowing the patient to change graphics/color settings in a dialysis system employing the embodiments discussed herein.

Referring now to FIGS. 17 to 19, different screen shots of video monitor 66 show different icons in combination with an up and down arrow 536. Up/down arrow 536 indicates that corresponding settings can be changed for a particular function indicated by its associated icon 520, 530 or 538. FIG. 17 for example shows glass 520, which if pressed allows the user to change characters, e.g., from a glass to a person, color of the character, e.g., blue to red, or shape of the character, e.g., glass as shown to a mug, for example. To these ends, any of the screens discussed herein can be associated with a touch screen overlay, which communicates with a touch screen controller, which in turn communicates directly or indirectly with a supervisory processor, controller or printed circuit board. Thus, glass 520 and arrow 536 can correspond to selectable areas or the touch screen. Alternatively, membrane switches or other types of electromechanical input devices are provided to enable the user to interact with glass 520 and arrow 536.

FIG. 18 shows arrow 536 operable with alarm 530. This screen enables the patient to change (as indicated by up and down arrow 536) the alarm settings. Alarm 530 can be colored yellow or red or otherwise brightly to indicate that the function is significant or to caution or warn the patient of a particular condition. FIG. 19 shows arrow 536 operable with a control panel 538. This screen allows the operator to change instrument settings, such as, volume settings, brightness settings and other user preferences relating to the operation of the dialysis machine.

Figure 20:
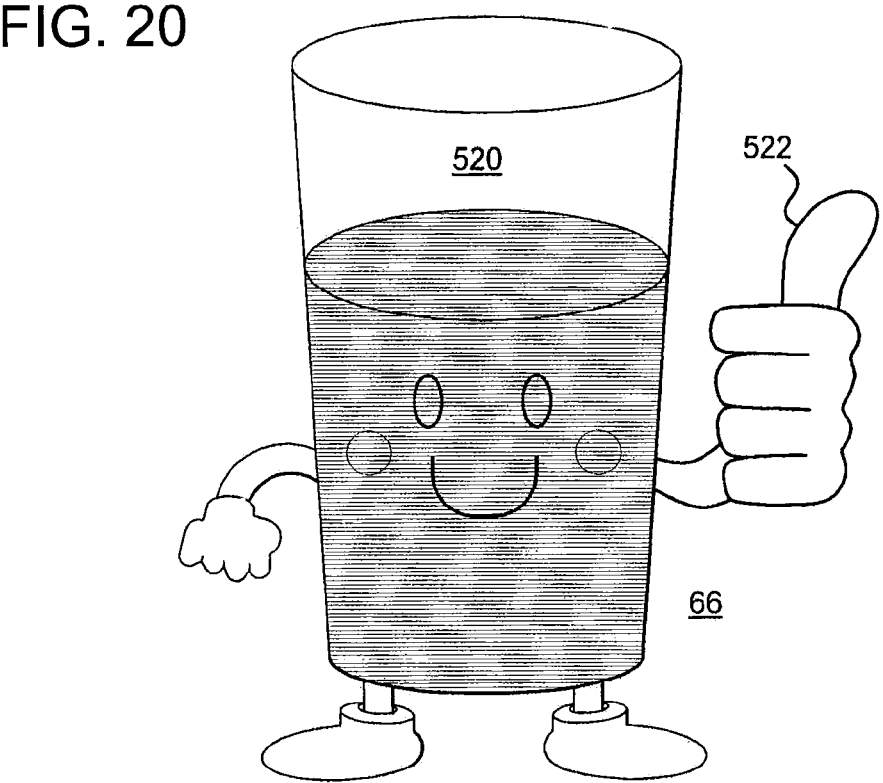
FIG. 20 is a machine screenshot illustrating an embodiment of a graphical depiction signifying that therapy has been successful for a dialysis system employing the embodiments discussed herein.
Figure 21:
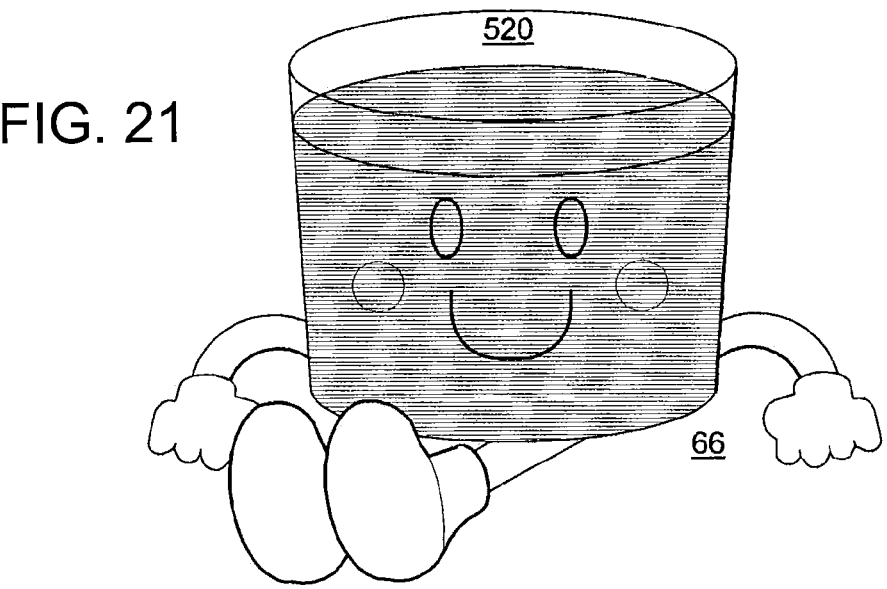
FIG. 21 is a machine screenshot illustrating an embodiment of a graphical depiction signifying that the machine has gone into a standby mode for a dialysis system employing the embodiments discussed herein.

Referring now to FIGS. 20 and 21, video monitor 66 illustrates character 520 at the end of therapy or cycle. FIG. 20 illustrates a therapy successfully completed screen. Here character 520 and character indicator 522 indicate that the previous treatment or treatment cycle has been completed successfully. FIG. 21 shows character 520 in a rest or sleep mode. Here, character 520 is indicating that the machine, while powered, is in a shut-down or dormant mode, in which therapy has ended or is in a paused or waiting state for a task to be completed or command to be entered.

Character 520 is shown above displaying parameters for a PD system. In an alternative embodiment, character 520 is used in a blood filtering dialysis therapy, such as, HD, HF or HDF. Here, character 520 can indicate ultrafiltration and the percentage of a prescribed amount of ultrafiltrate that has been removed at a certain point during treatment.

It should be understood that various changes and modifications to the presently preferred embodiments described herein will be apparent to those skilled in the art. Such changes and modifications can be made without departing from the spirit and scope of the present disclosure and without diminishing its intended advantages. It is therefore intended that such changes and modifications be covered by the appended claims.

The disclosure is claimed as follows:

1. A medical therapy machine comprising:
an enclosure;
a medical therapy machine component located inside the enclosure;
a video monitor supported by the enclosure and displaying at least one of information and indicia relating to the medical therapy;
an ambient light sensor attached to the enclosure and located in substantially the same plane as the video monitor, the ambient light sensor facing a same direction as the video monitor so as to avoid receiving light directly from the video monitor, the ambient light sensor sensing a level of ambient light impinging the video monitor; and
a logic implementor configured to control a level of backlight brightness for the video monitor based on the level of ambient light sensed by the sensor.

2. The medical therapy machine of claim 1, wherein the sensor includes a photoreceptor having a spectral response approximating that of a human eye.

3. The medical therapy machine of claim 1, wherein the logic implementor includes at least one of: a dedicated analog circuit, a dedicated digital circuit, a microcontroller, a hybrid circuit and microcontroller and a functional element of a shared applications processor.

4. The medical therapy machine of claim 1, which includes interface circuitry configured to interface an output of the sensor with the logic implementor.

5. The medical therapy machine of claim 1, which includes a manual brightness input device coupled operably to the logic implementor, the implementor and input device configured to enable a user of the machine to set an initial level of backlight brightness.

6. The medical therapy machine of claim 1, wherein the logic implementor is configured to do at least one of: (i) increase the level of backlight brightness for the video monitor when the sensor senses an increased level of ambient light; and (ii) decrease the level of backlight brightness for the video monitor when the sensor senses a decreased level of ambient light.

7. The medical therapy machine of claim 1, wherein the medical therapy machine is a peritoneal dialysis or hemodialysis machine.

8. The medical therapy machine of claim 1, wherein the video monitor is operable with a touch screen, the touch screen configured to provide at least one selectable input for controlling a parameter relating to the medical therapy, the logic implementor configured to control the level of backlight brightness for the at least one selectable input individually based on the level of ambient light sensed by the sensor.

9. The medical therapy machine of claim 1, which includes a keypad operable with the video monitor, the logic implementor configured to control the level of backlight brightness for the keypad based on the level of ambient light sensed by the sensor.

10. The medical therapy machine of claim 9, wherein the keypad includes a plurality of selectable buttons for controlling a parameter relating to the medical therapy, the logic implementor configured to selectively and individually backlight at least one of the buttons.

11. The medical therapy machine of claim 9, wherein the keypad includes a plurality of buttons, the display configured to show indicia relating to one of the buttons, the logic implementor configured to backlight the button while the indicia is shown on the video monitor.

12. A medical therapy machine comprising:
an enclosure;
a medical therapy machine component located inside the enclosure;
a video monitor supported by the enclosure;
a keypad supported by the enclosure and including a plurality of illuminated buttons, at least one of the buttons providing operator control of the medical therapy machine component;
an ambient light sensor attached to the enclosure and located in substantially the same plane as the video monitor, the ambient light sensor facing a same direction as the video monitor so as to avoid receiving light directly from the video monitor, the ambient light sensor sensing a level of ambient light impinging the video monitor; and
a logic implementor configured to control a level of backlight brightness for the illuminated buttons based on the level of ambient light sensed by the sensor.

13. The medical therapy machine of claim 12, wherein the logic implementor includes at least one of: a dedicated analog circuit, a dedicated digital circuit, a microcontroller, a hybrid circuit and microcontroller and a functional element of a shared applicator's processor.

14. The medical therapy machine of claim 12, which includes a manual brightness input device coupled operably to the logic implementor, the implementor and input device configured to enable a user of the machine to set an initial level of backlight brightness.

15. The medical therapy machine of claim 12, wherein the logic implementor is configured to do at least one of: (i) increase the level of backlight brightness for the illuminated buttons when the sensor senses an increased level of ambient light; and (ii) decrease the level of backlight brightness for the illuminated buttons when the sensor senses a decreased level of ambient light.

16. The medical therapy machine of claim 12, wherein at least one of the buttons includes at least one characteristic selected from the group consisting of: (i) having a three dimensional shape; (ii) being raised; (iii) having an associated unique icon inset from a surface of the button; (iv) being color-coded; (v) being individually capable of being backlit; (vi) being hidden and locatable via identifying markings on the keypad; (vii) being configured to provide tactile feedback when pressed; and (viii) being configured as at least one of an up and down parameter adjuster.

17. The medical therapy machine of claim 12, wherein the logic implementor is further configured to control the level of backlight brightness based on a person's natural night vision adjustment.

18. A medical therapy machine comprising:
an enclosure;
a medical therapy machine component located inside the enclosure;
a video display supported by the enclosure and displaying at least one of information and indicia relating to the medical therapy;
a keypad operable with the video display, the keypad including a plurality of buttons;
an ambient light sensor attached to the enclosure and located in substantially the same plane as the video display, the ambient light sensor facing a same direction as the video display so as to avoid receiving light directly from the video display, the ambient light sensor sensing a level of ambient light impinging the enclosure; and
a logic implementor configured to increase a level of backlight brightness for at least one of: (i) the display; and (ii) at least one of the buttons when a level of ambient light impinging the enclosure increases, wherein the level of backlight brightness of the video display is controlled independently from the level of backlight brightness of the at least one button.

19. The medical therapy machine of claim 18, wherein the logic implementor is configured to additionally compensate for a human eye's change in sensitivity due to the level of ambient light sensed over time.

20. The medical therapy machine of claim 18, wherein the logic implementor includes at least one of: a dedicated analog circuit, a dedicated digital circuit, a microcontroller, a hybrid circuit and microcontroller and a functional element of a shared applicator's processor.

21. The medical therapy machine of claim 18, wherein the medical therapy machine is a peritoneal dialysis or hemodialysis machine.

22. The medical therapy machine of claim 18, which includes interface circuitry configured to interface an output of the sensor with the logic implementor.

23. The medical therapy machine of claim 18, wherein the display is configured to show indicia relating to one of the buttons, the logic implementor configured to backlight the button while the indicia is shown on the display.

24. The medical therapy machine of claim 1, which includes a manual brightness input device coupled operably to the logic implementor, the logic implementor setting an initial level of backlight brightness for the video monitor, the logic implementor and input device configured to enable a user of the machine to override the initial level of backlight brightness for the video monitor.

25. The medical therapy machine of claim 5, wherein the logic implementor is configured to (i) initially set the level of backlight brightness for the video monitor to the initial level of backlight brightness set by the user and (ii) modify the level of backlight brightness for the video monitor based upon the level of ambient light sensed by the sensor.

26. The medical therapy machine of claim 1, wherein the logic implementor is further configured to control the level of backlight brightness for the video monitor based on a person's natural night vision adjustment by decreasing the level of backlight brightness over time when the ambient light sensor senses a pre-selected steady level of ambient light.

27. The medical therapy machine of claim 12, which includes a manual brightness input device coupled operably to the logic implementor, the logic implementor setting an initial level of backlight brightness for the illuminated buttons, the logic implementor and input device configured to enable a user of the machine to override the initial level of backlight brightness for the illuminated buttons.

28. The medical therapy machine of claim 14, wherein the logic implementor is configured to (i) initially set the level of backlight brightness for the illuminated buttons to the initial level of backlight brightness set by the user and (ii) modify the level of backlight brightness for the illuminated buttons based upon the level of ambient light sensed by the sensor.

29. The medical therapy machine of claim 17, wherein the logic implementor is configured to control the level of backlight brightness for the illuminated buttons based on a person's natural night vision adjustment by decreasing the level of backlight brightness over time when the ambient light sensor senses a pre-selected steady level of ambient light.

30. The medical therapy machine of claim 18, wherein the level of backlight brightness for the video display is one of (i) the same as the level of backlight brightness for the at least one of the keypad buttons, or (ii) controlled to be more or less bright than the level of backlight brightness for the at least one of the keypad buttons.

* * * * *